United States Patent
Kamatani et al.

(10) Patent No.: US 8,968,889 B2
(45) Date of Patent: Mar. 3, 2015

(54) ORGANIC COMPOUND AND ORGANIC LIGHT-EMITTING DEVICE

(75) Inventors: Jun Kamatani, Tokyo (JP); Kengo Kishino, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 351 days.

(21) Appl. No.: 13/634,372

(22) PCT Filed: Mar. 22, 2011

(86) PCT No.: PCT/JP2011/001678
§ 371 (c)(1),
(2), (4) Date: Sep. 12, 2012

(87) PCT Pub. No.: WO2011/121935
PCT Pub. Date: Oct. 6, 2011

(65) Prior Publication Data
US 2013/0002526 A1  Jan. 3, 2013

(30) Foreign Application Priority Data

Mar. 30, 2010  (JP) ................. 2010-078291

(51) Int. Cl.
*H01L 51/54* (2006.01)
*C07D 213/16* (2006.01)
(Continued)

(52) U.S. Cl.
CPC .............. *C07D 471/04* (2013.01); *C07C 13/62* (2013.01); *C07D 209/86* (2013.01); *C09K 11/06* (2013.01);
(Continued)

(58) Field of Classification Search
None
See application file for complete search history.

(56) References Cited

U.S. PATENT DOCUMENTS

2002/0168544 A1 * 11/2002 Fukuoka et al. ............... 428/690
2004/0076853 A1 * 4/2004 Jarikov ........................ 428/690

FOREIGN PATENT DOCUMENTS

JP    9-241629 A    9/1997
JP    11-255508 A   9/1999
(Continued)

*Primary Examiner* — Dawn L. Garrett
(74) *Attorney, Agent, or Firm* — Canon U.S.A., Inc. IP Division

(57) ABSTRACT

A novel organic compound suitable for emitting green light and an organic light-emitting device including the organic compound are provided. The organic compound is represented by general formula (1). In general formula (1), $R_1$ to $R_{18}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

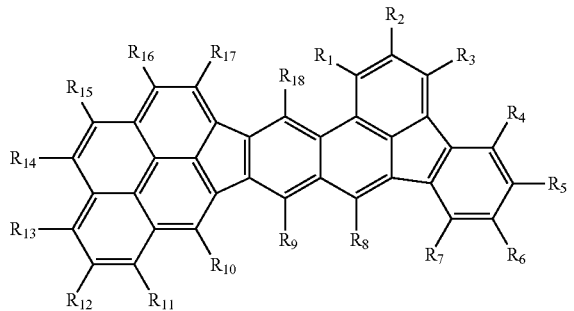

(1)

11 Claims, 1 Drawing Sheet

(51) Int. Cl.

| | | |
|---|---|---|
| *C07D 401/10* | (2006.01) | |
| *C07C 13/62* | (2006.01) | |
| *C07C 211/61* | (2006.01) | |
| *C07C 25/22* | (2006.01) | |
| *C07C 43/267* | (2006.01) | |
| *G09G 3/30* | (2006.01) | |
| *C07D 471/04* | (2006.01) | |
| *C07D 209/86* | (2006.01) | |
| *C09K 11/06* | (2006.01) | |
| *H05B 33/14* | (2006.01) | |
| *H01L 51/00* | (2006.01) | |
| *H01L 51/50* | (2006.01) | |

(52) U.S. Cl.
CPC ........ *H05B 33/14* (2013.01); *C09K 2211/1011* (2013.01); *H01L 51/0057* (2013.01); *H01L 51/0059* (2013.01); *H01L 51/0072* (2013.01); *H01L 51/5012* (2013.01); *Y10S 428/917* (2013.01)
USPC ........... 428/690; 428/917; 313/504; 313/506; 257/40; 546/255; 546/285; 564/426; 570/129; 568/632; 585/27; 345/76

(56) References Cited

FOREIGN PATENT DOCUMENTS

| | | |
|---|---|---|
| JP | 2008-290999 A | 12/2008 |
| JP | 2009-152529 A | 7/2009 |
| JP | 2009-302470 A | 12/2009 |
| JP | 2010-254610 A | 11/2010 |
| JP | 2010-270103 A | 12/2010 |
| JP | 2011-037744 A | 2/2011 |
| WO | 01/23497 A1 | 4/2001 |
| WO | 2010/013520 A1 | 2/2010 |

* cited by examiner

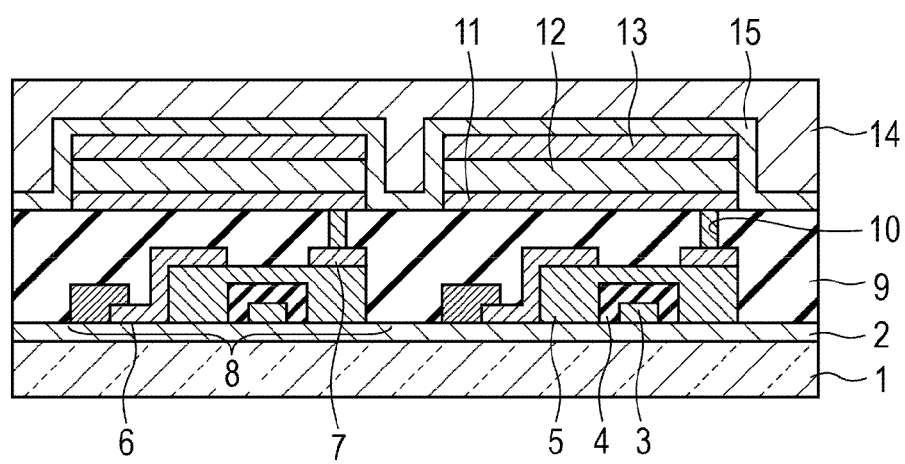

ORGANIC COMPOUND AND ORGANIC LIGHT-EMITTING DEVICE

TECHNICAL FIELD

The present invention relates to a novel organic compound and an organic light-emitting device including the same.

BACKGROUND ART

Organic light-emitting devices are devices including a pair of electrodes and an organic compound layer disposed between the pair of electrodes. By injecting electrons and holes from the electrodes, excitons of an organic compound are generated, and light is emitted when the excitons are returned to the ground state. Such organic light-emitting devices are also referred to as "organic electroluminescent devices" or "organic EL devices."

Heretofore, novel compounds have been actively developed. For example, as a compound used in a light-emitting layer, PTL 1 discloses compound IK-17 represented by the structural formula below. Compound IK-17 has a structure having benzo[k]fluoranthene as a basic structure and having a phenyl group at each of the 7-position and the 12-position of the benzo[k]fluoranthene. Herein, the term "basic structure" means a structure constituted by only a fused-ring structure.

[Chem. 1]

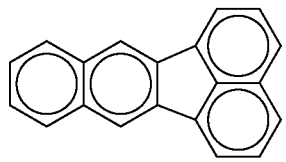

(Basic structure)

[Chem. 2]

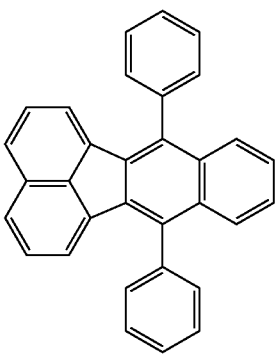

(IK-17)

CITATION LIST

Patent Literature

PTL 1: Japanese Patent Laid-Open No. 9-241629 (There is no corresponding foreign case.)

SUMMARY OF INVENTION

Compound IK-17 disclosed in PTL 1 emits blue light. Furthermore, this basic structure emits ultraviolet light, which has a wavelength shorter than that of blue light. It is believed that light having a longer wavelength can be emitted by introducing a substituent into this basic structure. Green light can be emitted by introducing some types of substituents. However, introducing a substituent may impair the stability of the compound.

The present invention provides a novel organic compound in which light in the green range can be emitted by the basic structure itself.

Specifically, the present invention provides an organic compound represented by general formula (1) below.

[Chem. 3]

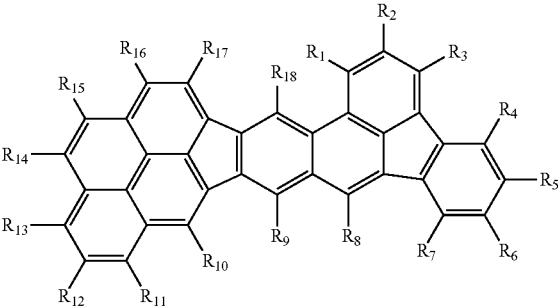

(1)

In general formula (1), $R_1$ to $R_{18}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

According to the present invention, since the basic structure itself has a wide band gap, it is possible to provide an organic compound in which light in the green range can be emitted by the basic structure itself. In addition, an organic light-emitting device including the novel organic compound can be provided.

BRIEF DESCRIPTION OF DRAWINGS

FIG. 1 is a schematic cross-sectional view showing organic light-emitting devices and switching devices connected to the organic light-emitting devices.

DESCRIPTION OF EMBODIMENTS

A novel organic compound according to the present invention is an organic compound represented by general formula (1) below.

[Chem. 4]

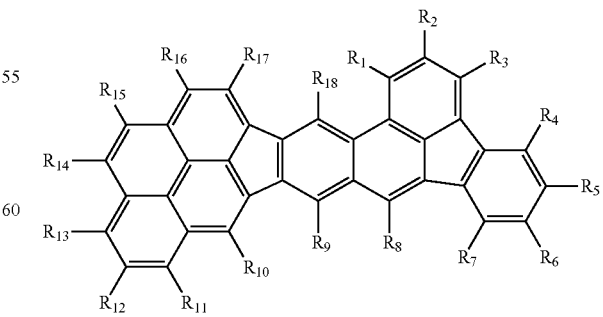

(1)

In general formula (1), $R_1$ to $R_{18}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

In general formula (1), examples of the alkyl group include, but are not limited to, a methyl group, an ethyl group, a n-propyl group, an isopropyl group, a n-butyl group, a tert-butyl group, a sec-butyl group, an octyl group, a 1-adamantyl group, and a 2-adamantyl group.

In general formula (1), examples of the alkoxy group include, but are not limited to, a methoxy group, an ethoxy group, a propoxy group, a 2-ethyl-octyloxy group, a phenoxy group, a 4-tert-butylphenoxy group, a benzyloxy group, and a thienyloxy group.

In general formula (1), examples of the amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

In general formula (1), examples of the aryl group include, but are not limited to, a phenyl group, a naphthyl group, an indenyl group, a biphenyl group, a terphenyl group, and a fluorenyl group.

In general formula (1), examples of the heterocyclic group include, but are not limited to, a pyridyl group, an oxazolyl group, an oxadiazolyl group, a thiazolyl group, a thiadiazolyl group, a carbazolyl group, an acridinyl group, and a phenanthrolyl group.

In general formula (1), the above-mentioned substituent, i.e., the alkyl group, the alkoxy group, the amino group, the aryl group, or the heterocyclic group may have a substituent such as an alkyl group, e.g., a methyl group, an ethyl group, or a propyl group; an aralkyl group, e.g., a benzyl group; an aryl group, e.g., a phenyl group or a biphenyl group; a heterocyclic group, e.g., a pyridyl group or a pyrrolyl group; an amino group, e.g., a dimethylamino group, a diethylamino group, a dibenzylamino group, a diphenylamino group, or a ditolylamino group; an alkoxyl group, e.g., a methoxyl group, an ethoxyl group, a propoxyl group, or a phenoxyl group; a cyano group; or a halogen atom, e.g., fluorine, chlorine, bromine, and iodine. However, the substituent is not limited thereto.

The inventors of the present invention focused on the basic structure itself. More specifically, the inventors of the present invention tried to provide a compound in which an emission wavelength of a molecule composed of only the basic structure falls within a desired emission wavelength range.

It is known that a substituent is introduced into a basic structure in order to obtain a desired emission wavelength. However, in such a case, the stability of the compound may be impaired.

In the present invention, the desired emission wavelength range is a green range, specifically, 480 nm or more and 530 nm or less.

In order to increase the quantum yield of an organic light-emitting device, it is desirable that a luminescent material itself have a high quantum yield. In order to achieve this, it is necessary for the luminescent material to satisfy the following conditions:

(I) The oscillator strength is high.

(II) An oscillating portion of the structure related to light emission is small.

As for the emission wavelength required for a material suitable for emitting green light in an organic light-emitting device, it is important that a solution of the luminescent material have an emission peak in the range of 480 nm or more and 530 nm or less.

As for (I) above, it is important to increase the symmetry of the structure of the luminescent material, the structure related to the light emission. This is because, in a molecule having high symmetry, the directions of the transition dipole moment of respective atoms can be easily aligned, and thus the transition dipole moment increases. A large transition dipole moment leads to a large oscillator strength, and the large oscillator strength leads to a high quantum yield.

Furthermore, by extending conjugation in one direction, the transition dipole moment of the molecule is increased to improve the oscillator strength. In this respect, the organic compound according to the present invention has a fused-ring structure in which conjugation is extended from the 8-position to the 10-position of benzo[k]fluoranthene. This structure leads to a further increase in the transition dipole moment as compared with that of benzo[k]fluoranthene. As a result, the organic compound according to the present invention has a structure with a high oscillator strength.

As for (II) above, when the structure related to light emission does not have a rotational structure, a change of energy that is obtained by the organic compound to kinetic energy such as rotational energy or vibrational energy is suppressed. As a result, it is possible to increase the proportion of energy that is released as photons. That is, a decrease in the quantum yield can be suppressed.

Comparison with Another Organic Compound

An organic compound of the present invention will be compared with benzo[k]fluoranthene, which is an analogous compound. The wavelength at which the intensity of a spectrum becomes maximum was compared between 7,12-diphenylbenzo[k]fluoranthene in which each of the 7-position and the 12-position of benzo[k]fluoranthene is substituted with a phenyl group and compound 1 which is an organic compound according to the present invention. The spectrum of the former compound had a maximum intensity at 428 nm. This does not correspond to light emission in the green range. In contrast, the spectrum of compound 1 had a maximum intensity at 488 nm. Thus, compound 1 emits light in the green range.

[Chem.5]

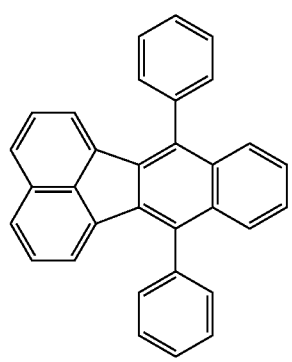

7,12-Diphenylbenzo[k]fluoranthene

[Chem.6]

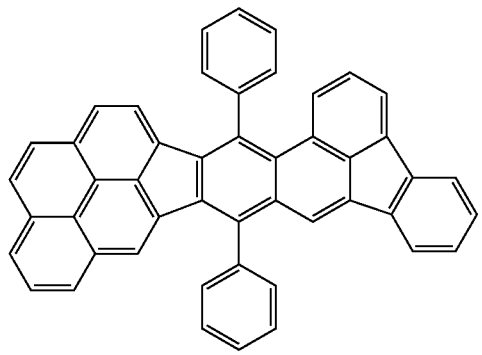

Compound 1

Even only the basic structure of the organic compound according to the present invention can emit light in the green range, and achieves a high quantum yield.

Furthermore, since the organic compound according to the present invention has two five-membered ring structures in the basic structure thereof, the energy levels of the highest occupied molecular orbital (HOMO) and lowest unoccupied molecular orbital (LUMO) are lower (deeper with respect to the vacuum level) than those of compounds having one five-membered ring structure. An organic compound having a low oxidation potential requires larger energy to be oxidized, and thus such a compound is stable against oxidation. When the organic compound according to the present invention is used as a luminescent material, the organic compound is suitable as an electron-trapping luminescent material. The electron-trapping luminescent material refers to a luminescent material in which the LUMO level of a luminescent material that performs main light emission is lower than the LUMO level of a material of a layer adjacent to the cathode side of a light-emitting layer. In this case, deficiency of electrons in the luminescent material that performs main light emission can be suppressed.

In addition, the basic structure of the organic compound according to the present invention contains no heteroatom such as a nitrogen atom. This also contributes to a low oxidation potential. That is, this also contributes to the stability of the organic compound against oxidation. It is also preferable that the substituents of the organic compound contain no heteroatom.

The basic structure of the organic compound according to the present invention has a low HOMO energy level. That is, the LUMO energy level of the basic structure is also low. When the LUMO energy level is low, the injection barrier of electrons from the cathode is small, and thus electrons are easily injected.

The organic compound according to the present invention is used as a guest material or a host material of a light-emitting layer. The organic compound according to the present invention may be used in any layer other than the light-emitting layer, namely, a hole injection layer, a hole-transporting layer, a hole/exciton-blocking layer, an electron-transporting layer, or an electron injection layer.

The organic compound according to the present invention can be preferably used as a guest material of a light-emitting layer of an organic light-emitting device. In particular, the organic compound is preferably used as a guest material of a green-light-emitting device.

By introducing, into the basic structure of the organic compound according to the present invention, a substituent that shifts the emission wavelength to the long-wavelength side, a red-light-emitting material can also be provided. According to such a material having a basic structure into which a substituent that shifts the emission wavelength to the long-wavelength side is introduced, since the material has the basic structure according to the present invention, the material is stable against oxidation. Examples of the substituent that shifts the emission wavelength to the long-wavelength side include aryl groups, heterocyclic groups, and amino groups.

Preferably, the organic compound according to the present invention is used as a guest material of a light-emitting layer, and a host material having an energy level of the LUMO higher than that of this organic compound, in other words, a host material having an energy level of the LUMO closer to the vacuum level is used. This is because, since the organic compound of the present invention has a low LUMO, the organic compound can more satisfactorily receive electrons from the host material, the electrons being supplied to the light-emitting layer, i.e., the host material.

According to the organic compound according to the present invention, the basic structure itself has a wide band gap of 2.4 eV. Therefore, the organic compound according to the present invention can also be used as a host material of a yellow-light-emitting layer or a red-light-emitting layer.

The light-emitting layer may include one type of compound. Alternatively, the light-emitting layer may include a plurality of compounds such as a host material and a guest material.

In this embodiment, the term "host material" refers to a material having the highest weight ratio among compounds constituting a light-emitting layer. The term "guest material" refers to a material that has a weight ratio lower than that of the host material and that performs main light emission among the compounds constituting the light-emitting layer. The term "assist material" refers to a material that has a weight ratio lower than that of the host material and assists the light emission of the guest material among the compounds constituting the light-emitting layer.

Exemplification of Organic Compound According to the Present Invention

Specific examples of the compounds represented by general formula (1) above are shown below. However, the present invention is not limited thereto.

[Chem.7]

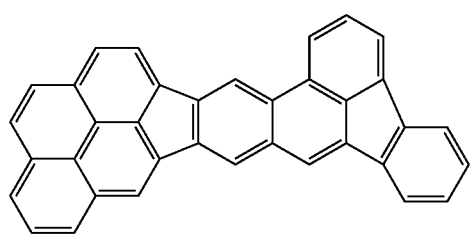

A1

A2
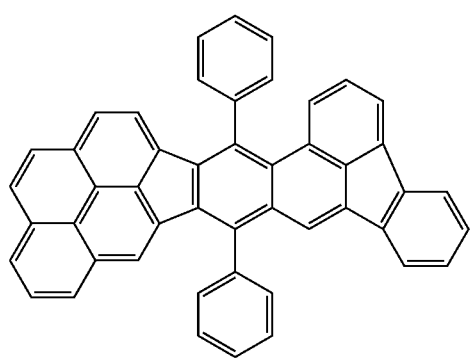
A3
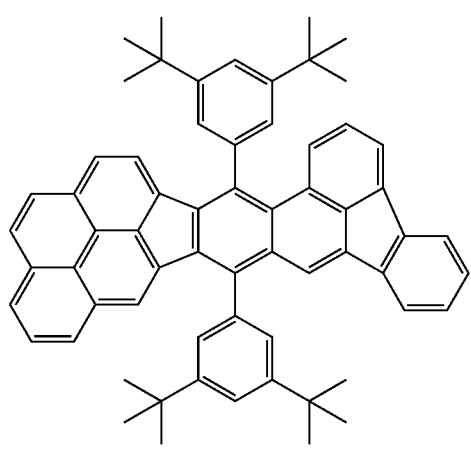
A4
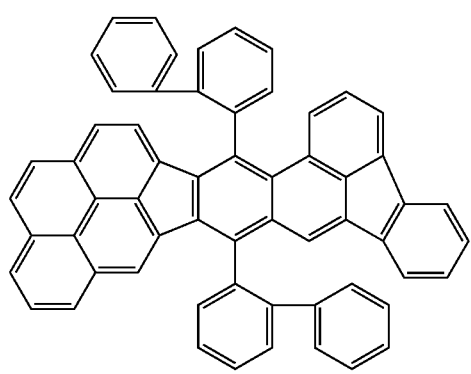
A5
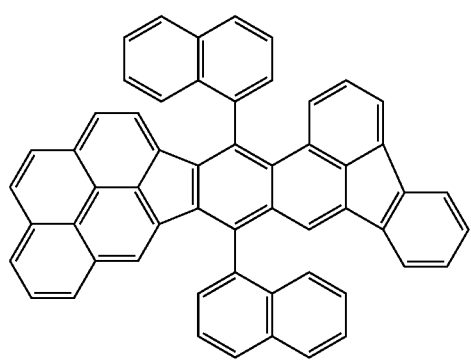
A6
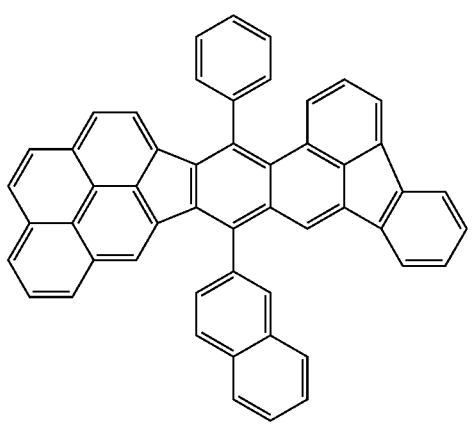
A7
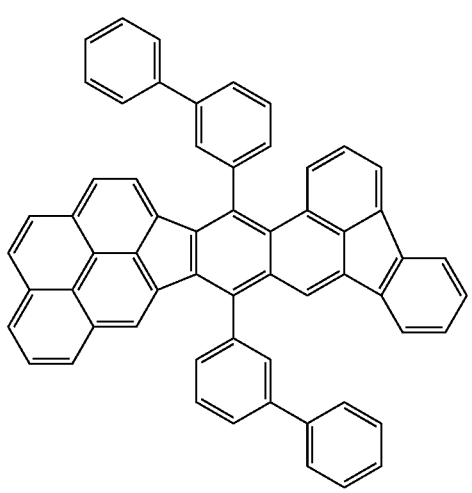
A8
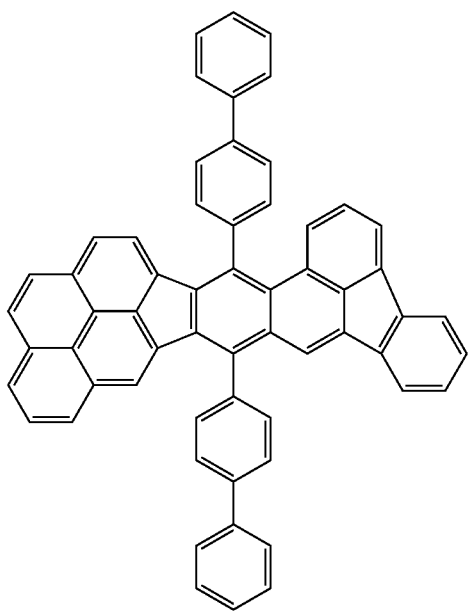

A9
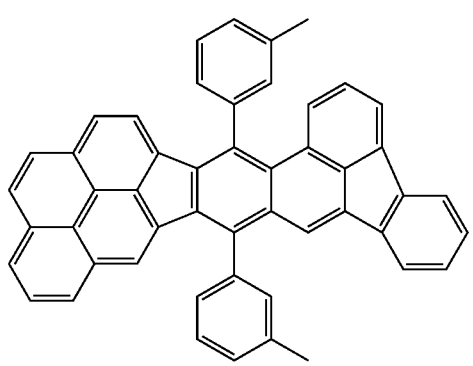
A12
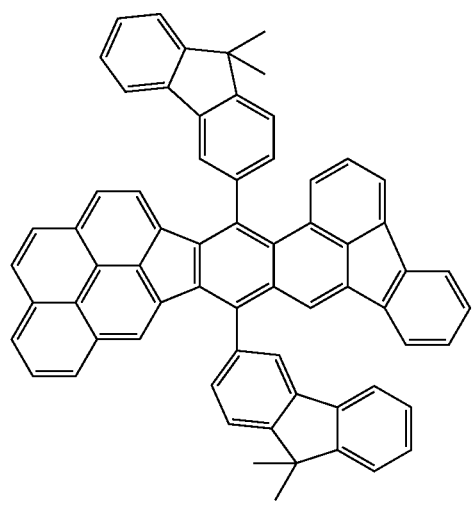
A10
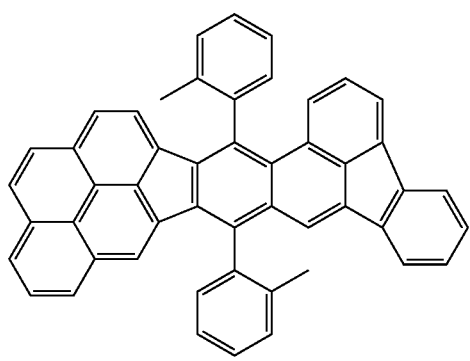
A13
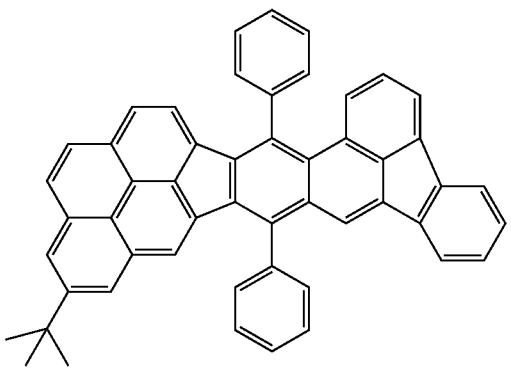
A11
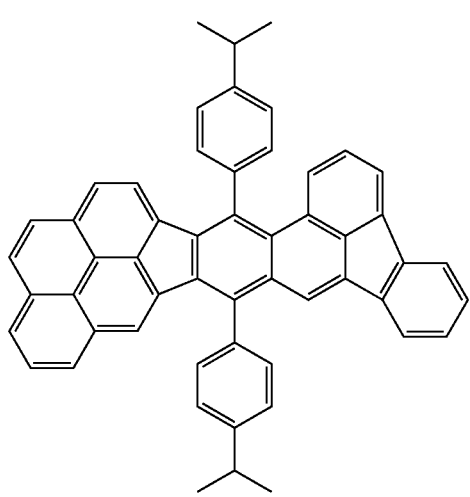
A14
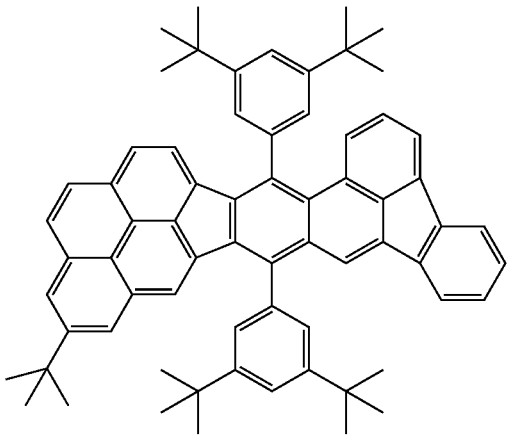

-continued
A15
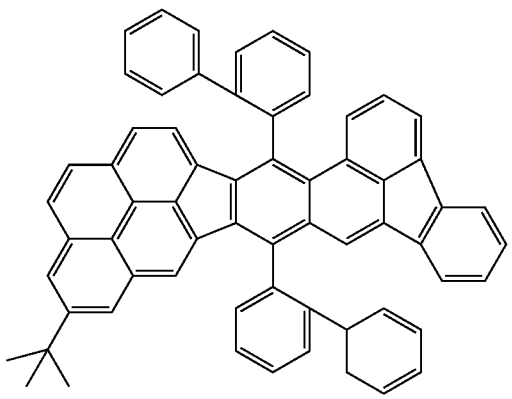
A16
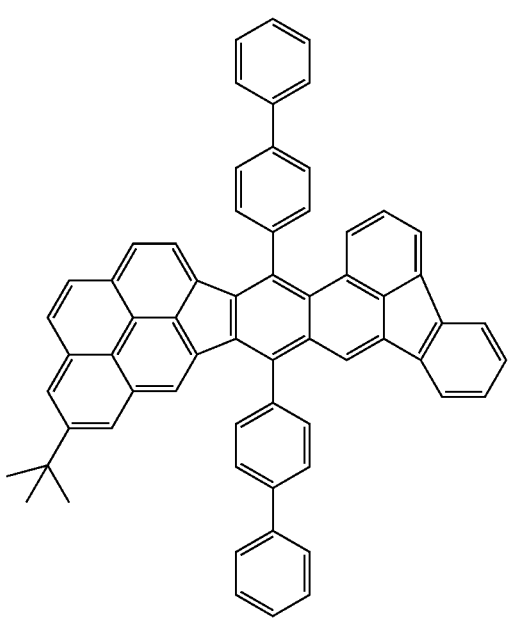
A17
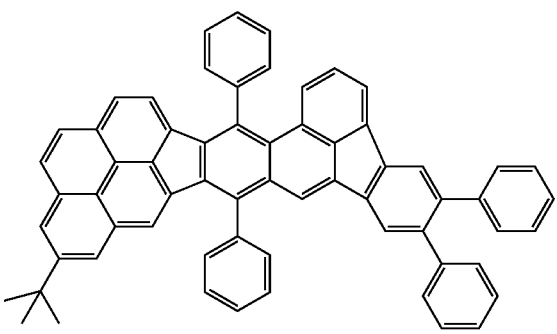
-continued
A18
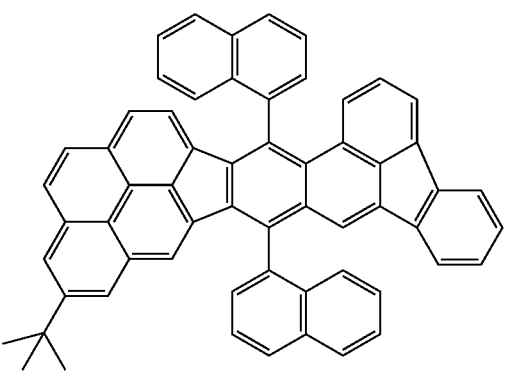
A19
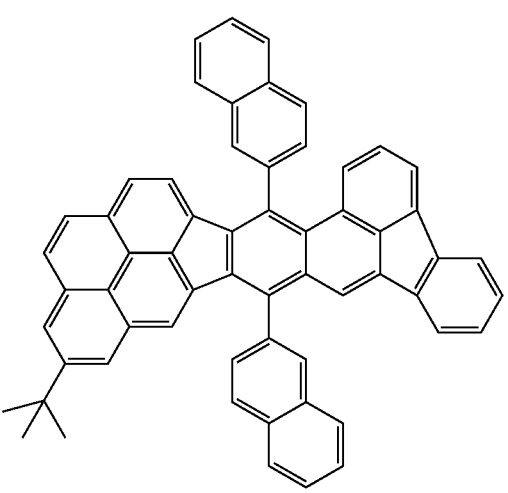
A20
A21
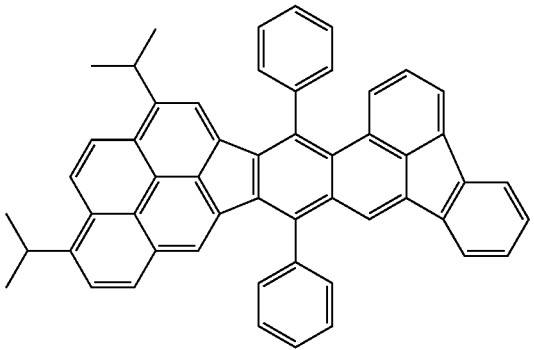

-continued
A22
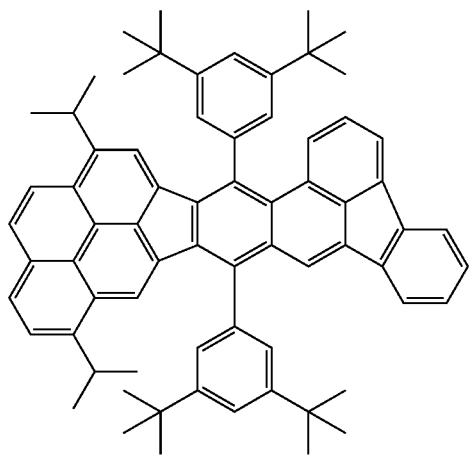
A23
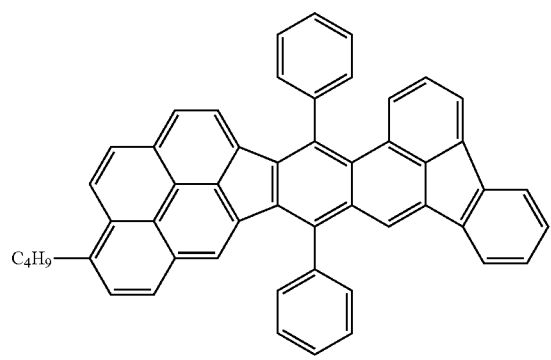
[Chem.8]
A24
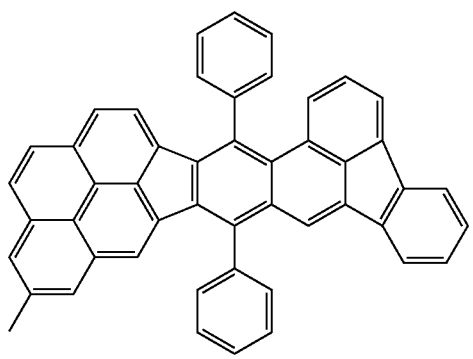
-continued
A26
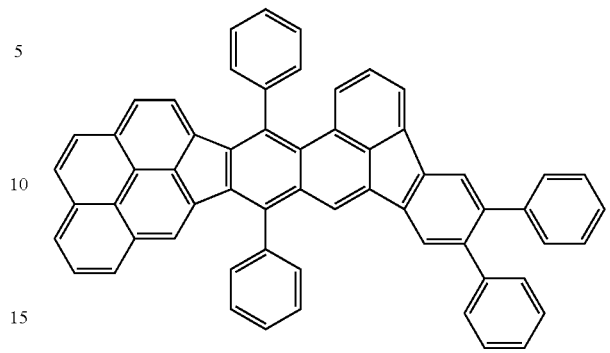
A27
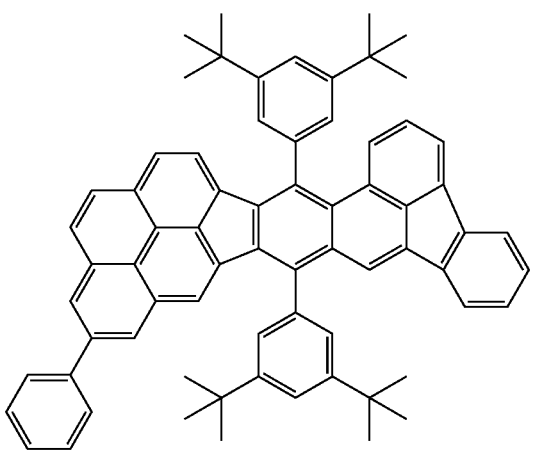
A28
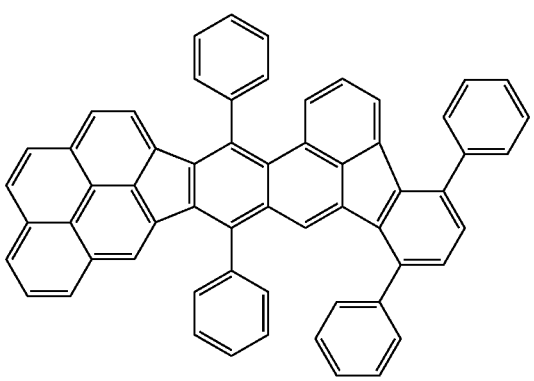
A25
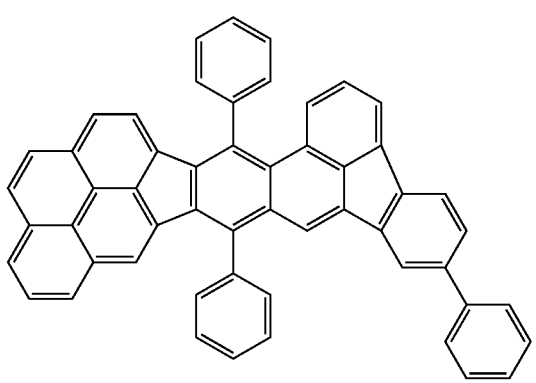
A29
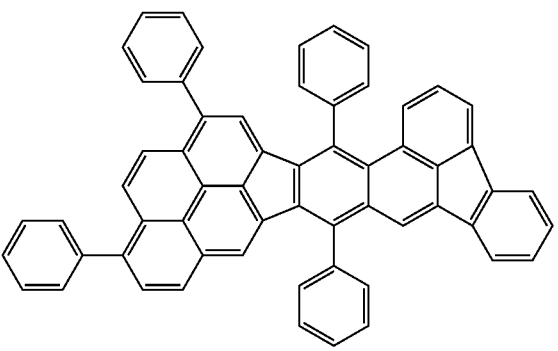

A30
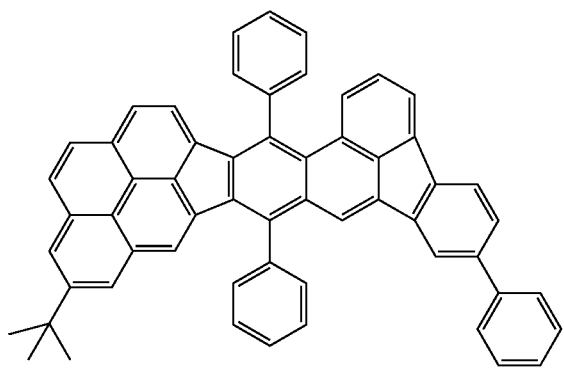
A31
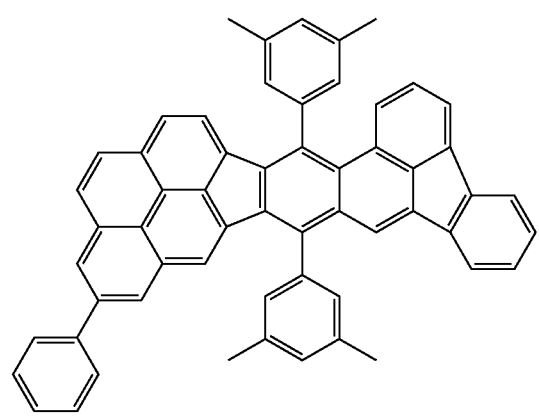
A32
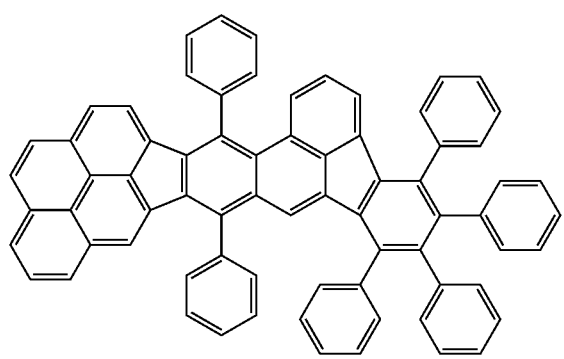
B1
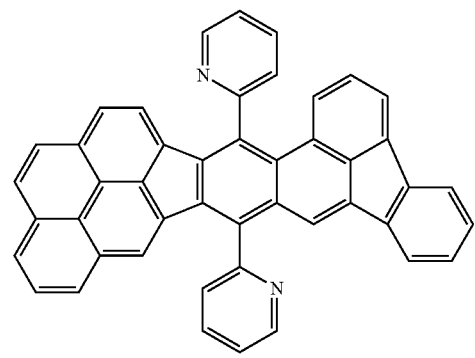
B2
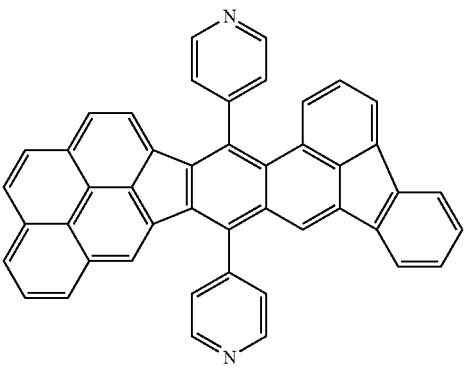
B3
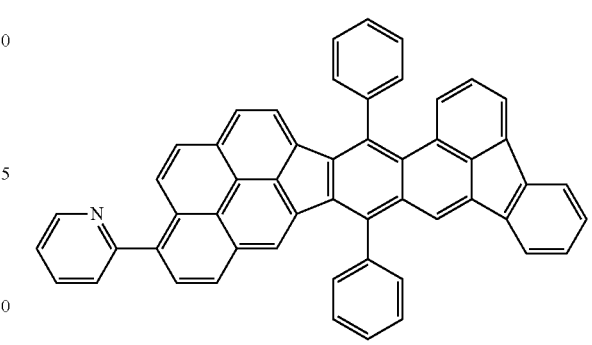
B4
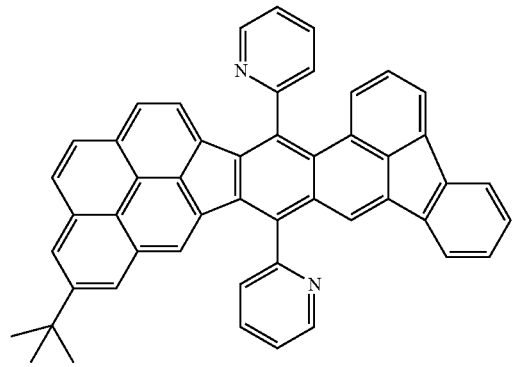
B5
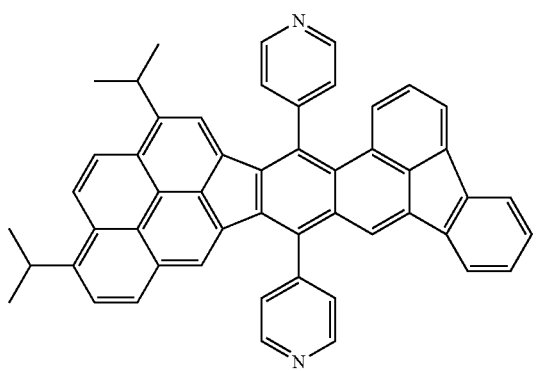

B6
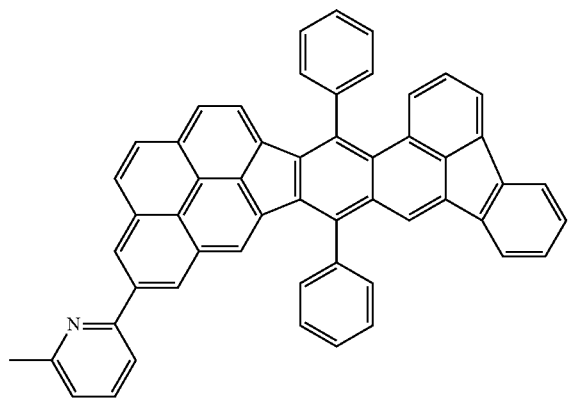

B7
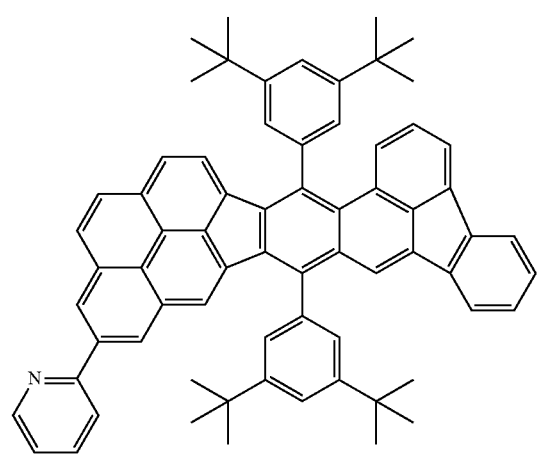

B8
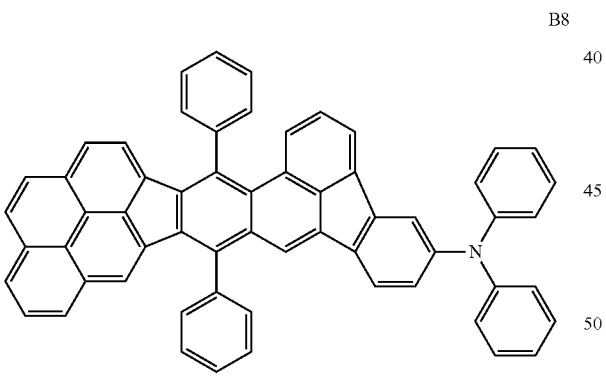

C1
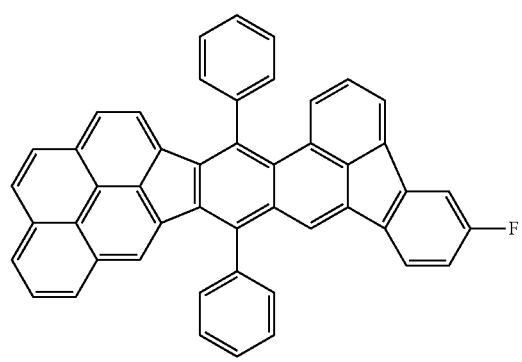

C2
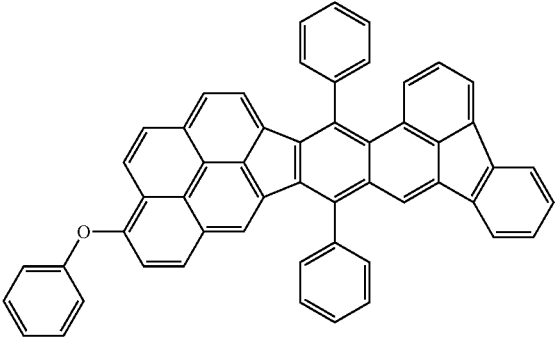

C3
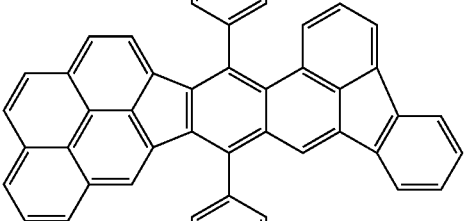

C4
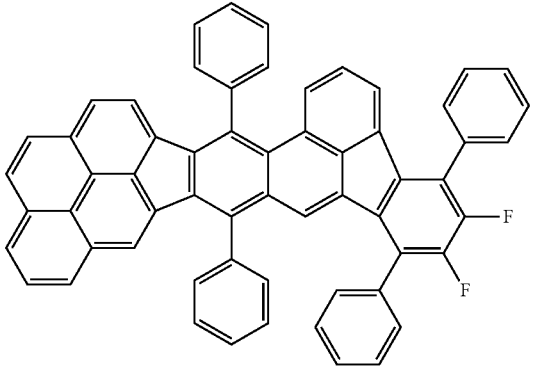

Properties of Respective Exemplified Compound Groups

Among the exemplified compounds, the whole molecule of each compound shown in group A consists of only a hydrocarbon. Compounds consisting of only hydrocarbons have low HOMO energy levels. Accordingly, the oxidation potentials are low, which indicates that the organic compounds are stable against oxidation.

Accordingly, among the organic compounds according to the present invention, the compounds shown in group A consisting of only hydrocarbons are preferable because the stability of their molecules is high.

Some of the compounds of group A are compounds represented by general formula (2) below. Organic compounds according to the present invention are more preferably represented by general formula (2) below.

[Chem. 9]

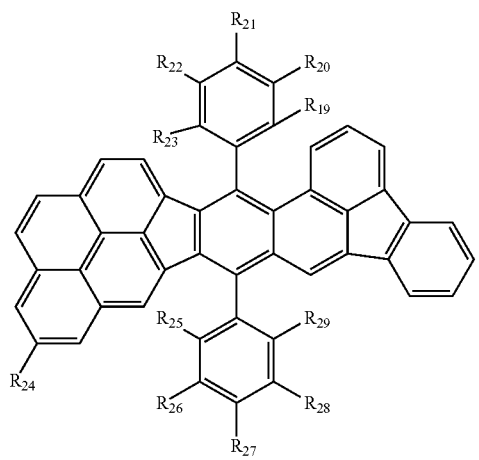

(2)

In general formula (2), $R_{19}$ to $R_{29}$ are each independently selected from an alkyl group and an aryl group.

This alkyl group is an alkyl group having 1 to 4 carbon atoms. Specifically, the alkyl group is a methyl group, an ethyl group, a n-propyl group, an isopropyl group, a n-butyl group, an isobutyl group, a sec-butyl group, or a tert-butyl group. A tert-butyl group is preferable because the tert-butyl group has an effect of suppressing molecular association by the steric hindrance.

This aryl group is a phenyl group, a naphthyl group, or a fluorenyl group. This is because these aryl groups are substituents suitable for shifting the emission wavelength to the long-wavelength side by about several nanometers to 20 nm in controlling the emission wavelength. The aryl group may further have a substituent. The substituent is an alkyl group having 1 to 4 carbon atoms or a phenyl group.

The two phenyl groups bonded to the basic structure in general formula (2) are substituents that suppress concentration quenching. When these phenyl groups have substituents, the effect of suppressing concentration quenching is further increased.

On the other hand, when a substituent contains a nitrogen atom as shown by the compounds in group B, the oxidation potential of the molecule significantly changes or the intermolecular interaction changes. When a substituent contains a nitrogen atom, the wavelength at which the intensity of a spectrum becomes maximum can be shifted to the long-wavelength side. Since the intermolecular interaction changes, in the case where a substituent contains a nitrogen atom, the compound can be used as an electron-transporting layer, a hole-transporting layer, or a light-emitting layer in a concentration of 100%.

Also, when a substituent contains a heteroatom other than a nitrogen atom as shown by the compounds in group C, the oxidation potential of the molecule also significantly changes or the intermolecular interaction changes. In some cases, a change more significantly than the case where a substituent contains a nitrogen atom can be expected. Since the intermolecular interaction changes, in the case where a substituent contains a heteroatom, the compound can be used as an electron-transporting layer, a hole-transporting layer, or a light-emitting layer in a concentration of 100%.

Exemplary compounds of group A to group C have been described. In these compounds, the basic structure itself can emit green light. In addition, when a substituent is introduced into the basic structure of the organic compound according to the present invention, the emission wavelength is shifted from green to the longer wavelength side. More specifically, such a substituted basic structure can emit red light. Furthermore, the application of the organic compound according to the present invention is not limited to a guest material of a light-emitting layer of an organic light-emitting device. Alternatively, the organic compound according to the present invention may be used as a host material of a light-emitting layer of an organic light-emitting device. Alternatively, the organic compound may be used in an electron-transporting layer, an electron injection layer, a hole-transporting layer, a hole injection layer, or a hole-blocking layer, or the like of an organic light-emitting device. In such a case, the luminescent color emitted by the organic light-emitting device is not limited. Furthermore, the organic compound according to the present invention can also be used as an assist material or a host material of a light-emitting layer of an organic light-emitting device that emits red light.

Description of Synthetic Route

An example of a synthetic route of the organic compound according to the present invention will be described. A reaction formula of the synthetic route is shown below. In the synthetic route shown by the reaction formula below, in the case where a substituent is introduced, the synthesis can be conducted while a hydrogen atom located at a position to be substituted is substituted with the target substituent. Examples of the substituent to be introduced include an alkyl group, a halogen atom, and a phenyl group.

Synthetic Route 1

[Chem. 10]

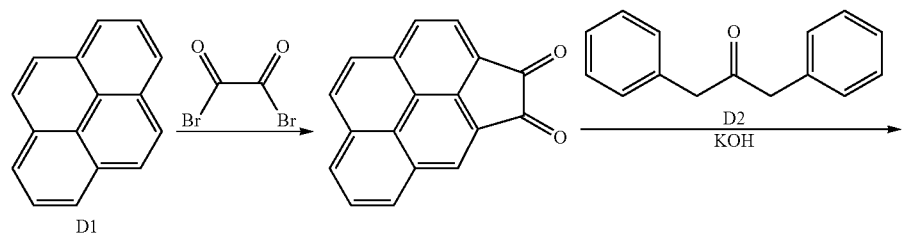

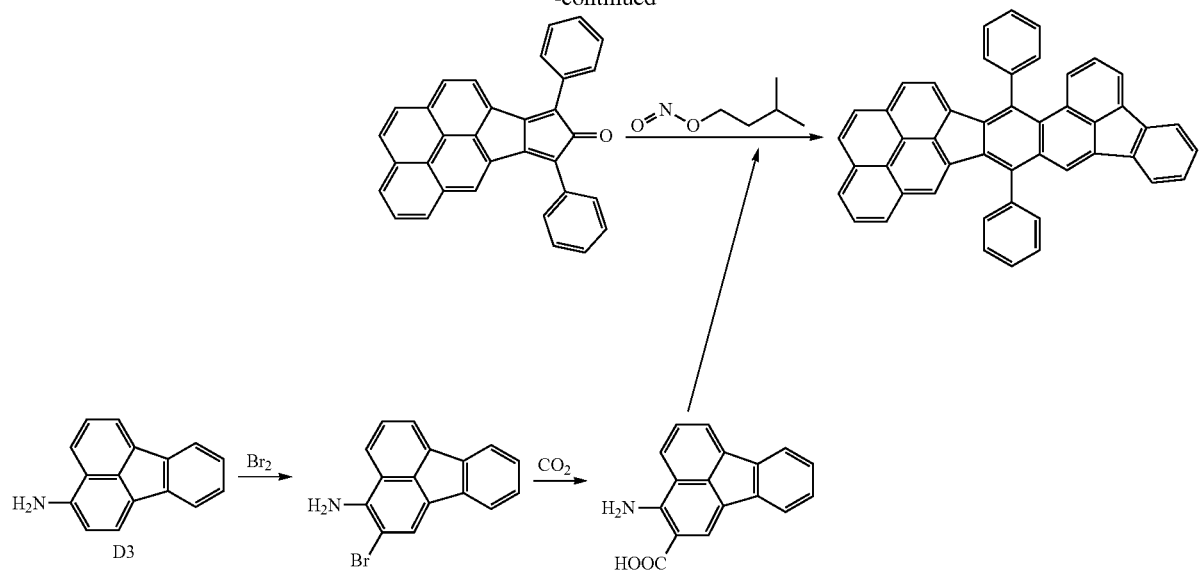

Other Organic Compounds and Starting Materials

Various compounds can be synthesized by changing compounds D1 to D3 in the above reaction formula. Specific examples of the compounds are shown in Table 1 as synthesized compounds. Table 1 also shows compounds D1 to D3 which are starting materials used for obtaining the synthesized compounds.

TABLE 1

| | D1 | D2 | D3 |
|---|---|---|---|
| Synthesis Example 1 | | | |
| Synthesis Example 2 | | | |
| Synthesis Example 3 | | | |
| Synthesis Example 4 | | | |

TABLE 1-continued
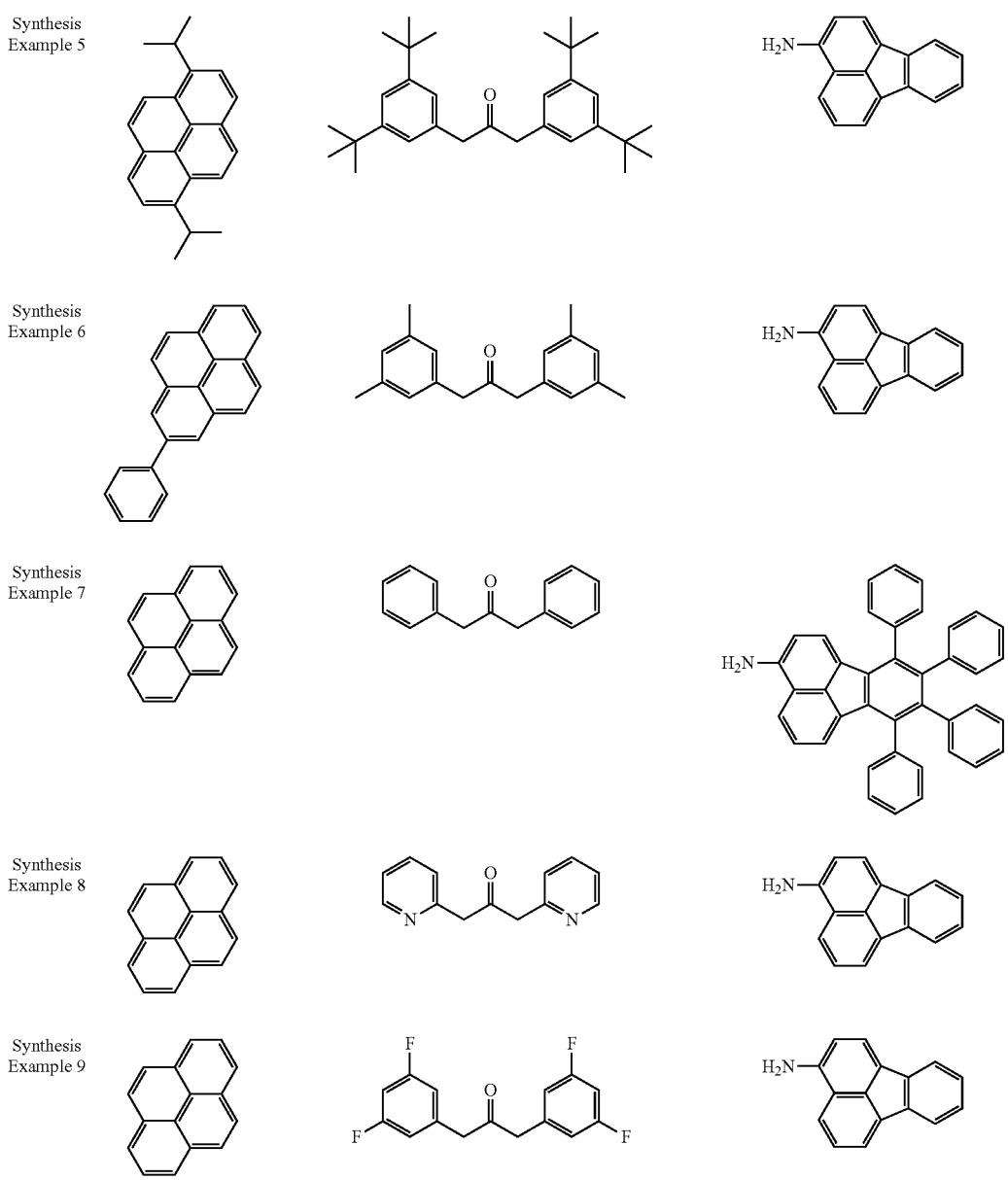
| | Synthesized compound | Exemplary compound No. |
|---|---|---|
| Synthesis Example 1 | 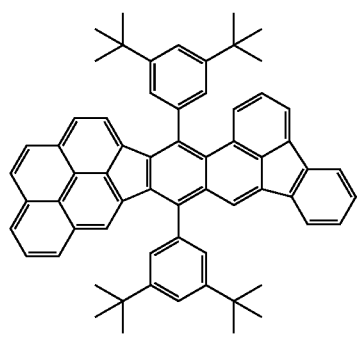 [SMILES: CC(C)(C)c1cc(-c2c3cc4c5ccccc5c5cccc(c3c(-c3cc(C(C)(C)C)cc(C(C)(C)C)c3)c3c6ccc7ccc8cccc9cc(c23)c6c7c89)c54)cc(C(C)(C)C)c1] | A3 |

TABLE 1-continued
| | | |
|---|---|---|
| Synthesis Example 2 | 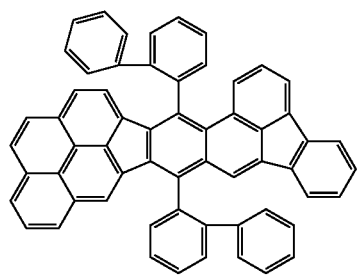 [SMILES: c1ccc(-c2ccccc2-c2c3cc4c5ccccc5c5cccc(c3c(-c3ccccc3-c3ccccc3)c3c6ccc7ccc8cccc9cc(c23)c6c7c89)c54)cc1] | A4 |
| Synthesis Example 3 | 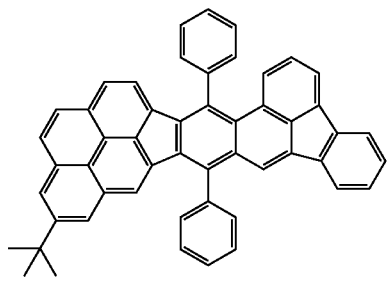 [SMILES: CC(C)(C)c1cc2ccc3ccc4c5c(-c6ccccc6)c6c(cc7c8ccccc8c8cccc6c87)c(-c6ccccc6)c5c5cc(c1)c2c3c54] | A13 |
| Synthesis Example 4 | 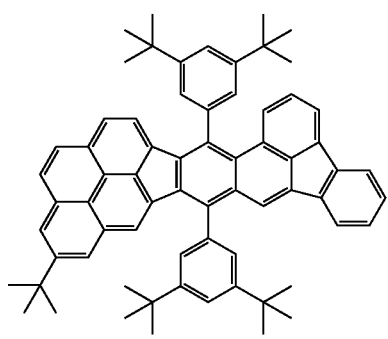 [SMILES: CC(C)(C)c1cc(-c2c3cc4c5ccccc5c5cccc(c3c(-c3cc(C(C)(C)C)cc(C(C)(C)C)c3)c3c6ccc7ccc8cc(C(C)(C)C)cc9cc(c23)c6c7c89)c54)cc(C(C)(C)C)c1] | A14 |
| Synthesis Example 5 | 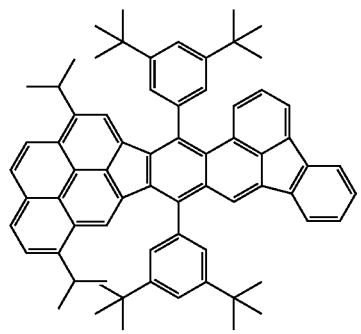 [SMILES: CC(C)c1ccc2ccc3c(C(C)C)cc4c5c(-c6cc(C(C)(C)C)cc(C(C)(C)C)c6)c6c(cc7c8ccccc8c8cccc6c87)c(-c6cc(C(C)(C)C)cc(C(C)(C)C)c6)c5c5cc1c2c3c54] | A22 |
| Synthesis Example 6 | 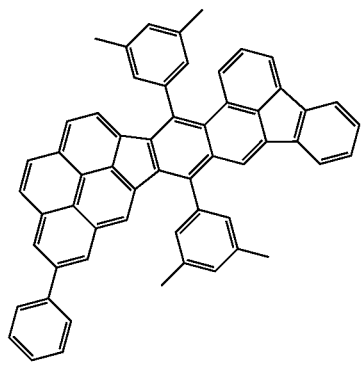 [SMILES: Cc1cc(C)cc(-c2c3cc4c5ccccc5c5cccc(c3c(-c3cc(C)cc(C)c3)c3c6ccc7ccc8cc(-c9ccccc9)cc9cc(c23)c6c7c89)c54)c1] | A31 |

TABLE 1-continued

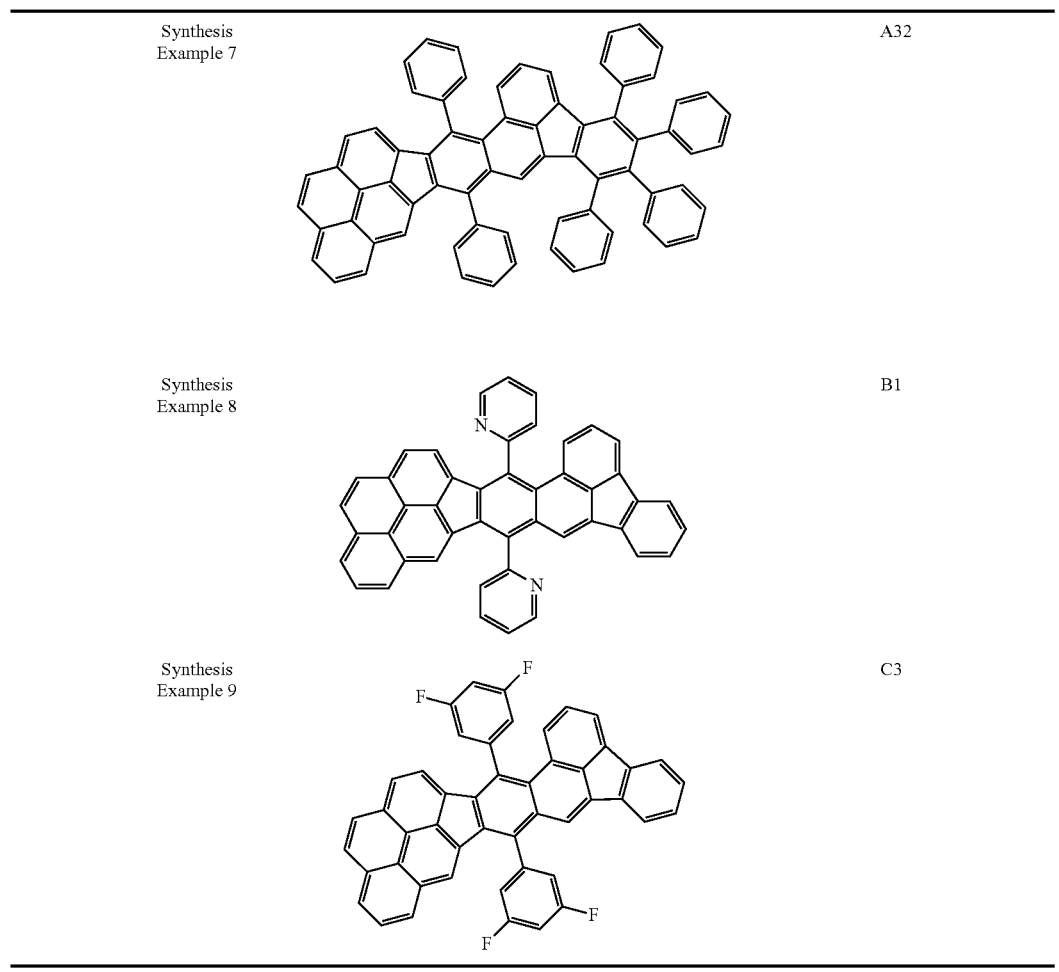

Synthesis Example 7 — A32

Synthesis Example 8 — B1

Synthesis Example 9 — C3

Organic Light-Emitting Device

An organic light-emitting device according to this embodiment will be described. The organic light-emitting device according to this embodiment includes a pair of electrodes, namely, an anode and a cathode, and an organic compound layer disposed between the anode and the cathode. This organic compound layer is a device including the organic compound according to the present invention.

The organic light-emitting device according to this embodiment may include a plurality of organic compound layers. Examples of these plurality of layers include a hole injection layer, a hole-transporting layer, a light-emitting layer, a hole-blocking layer, an exciton-blocking layer, an electron transporting layer, and an electron-injection layer. These layers can be appropriately used in combination.

When the organic compound according to this embodiment is used as a guest material in a light-emitting layer, the concentration of the guest material to a host material is preferably 0.1% by weight or more and 30% by weight or less, and more preferably 0.5% by weight or more and 10% by weight or less.

The inventors of the present invention have conducted various studies and found that a device in which the organic compound according to the present invention is used as a host material or a guest material, in particular, a guest material of a light-emitting layer had an optical output with a high quantum yield and a high luminance, and had high durability.

In the organic light-emitting device according to this embodiment, besides the organic compound according to the present invention, publicly known low-molecular weight and high-molecular weight hole injection materials, hole-transporting materials, host materials, guest materials, electron injection materials, electron-transporting materials, and the like can also be used in combination according to need.

Examples of the compounds will be described.

As materials used as a hole injection layer or a hole-transporting layer, materials having a high hole mobility are preferably used. Examples of the low-molecular weight and high-molecular weight materials having a hole injection performance or a hole transport performance include, but are not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

Table 2 shows specific structural formulae of the host materials. The host materials may be derivatives of the compounds represented by the structural formulae shown in Table 2. Examples of the host materials further include, but are not limited to, fused-ring compounds (such as fluorene derivatives, naphthalene derivatives, anthracene derivatives, pyrene derivatives, carbazole derivatives, quinoxaline derivatives, and quinoline derivatives), organoaluminum complexes such as tris(8-quinolinolato)aluminum, organozinc complexes, triphenylamine derivatives, and polymer derivatives such as poly(fluorene) derivatives and poly(phenylene) derivatives.

TABLE 2
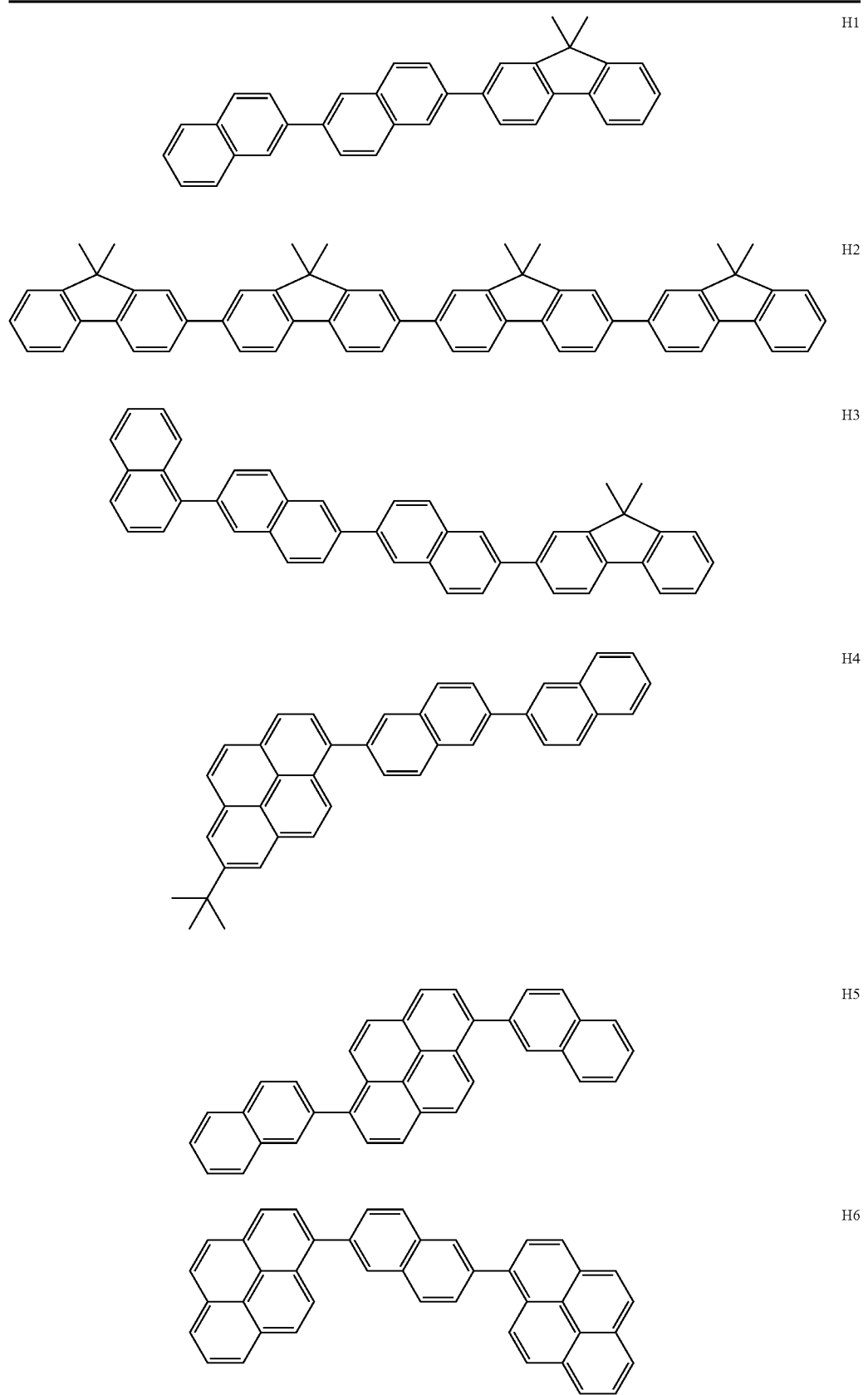

TABLE 2-continued
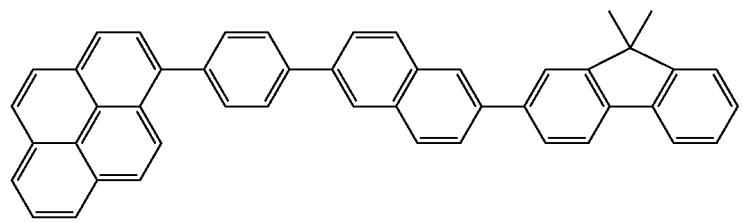 [SMILES: CC1(C)c2ccccc2-c2ccc(-c3ccc4cc(-c5ccc(-c6ccc7ccc8cccc9ccc6c7c89)cc5)ccc4c3)cc21]
H7
H8
H9
H10
H11

TABLE 2-continued
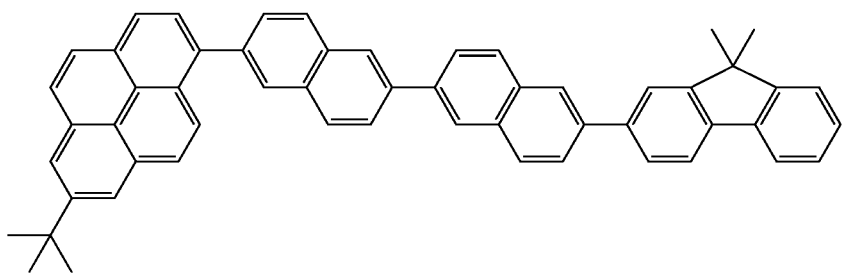 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
H12
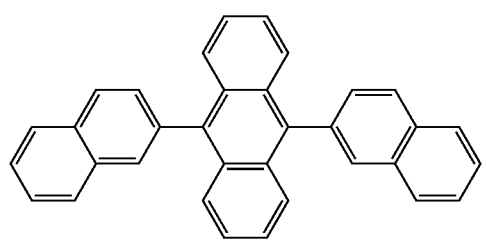 [SMILES: c1ccc2cc(-c3c4ccccc4c(-c4ccc5ccccc5c4)c4ccccc34)ccc2c1]
H13
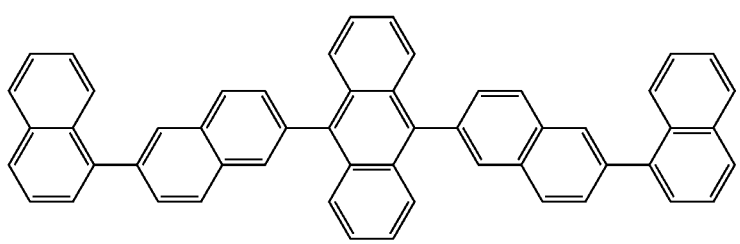 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H14
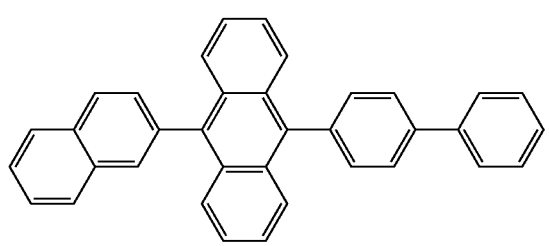 [SMILES: c1ccc(-c2ccc(-c3c4ccccc4c(-c4ccc5ccccc5c4)c4ccccc34)cc2)cc1]
H15
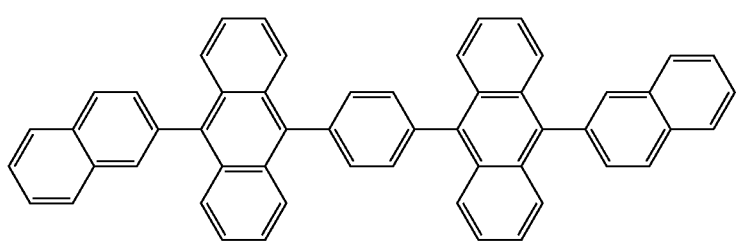 [SMILES: c1ccc2cc(-c3c4ccccc4c(-c4ccc(-c5c6ccccc6c(-c6ccc7ccccc7c6)c6ccccc56)cc4)c4ccccc34)ccc2c1]
H16
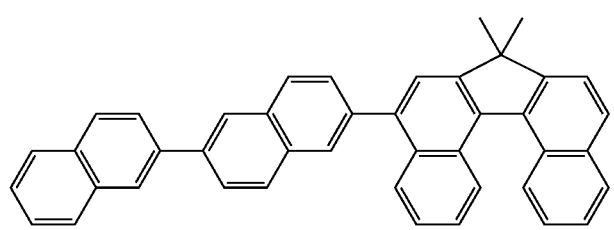 [SMILES: CC1(C)c2ccc3ccccc3c2-c2c1cc(-c1ccc3cc(-c4ccc5ccccc5c4)ccc3c1)c1ccccc21]
H17

TABLE 2-continued
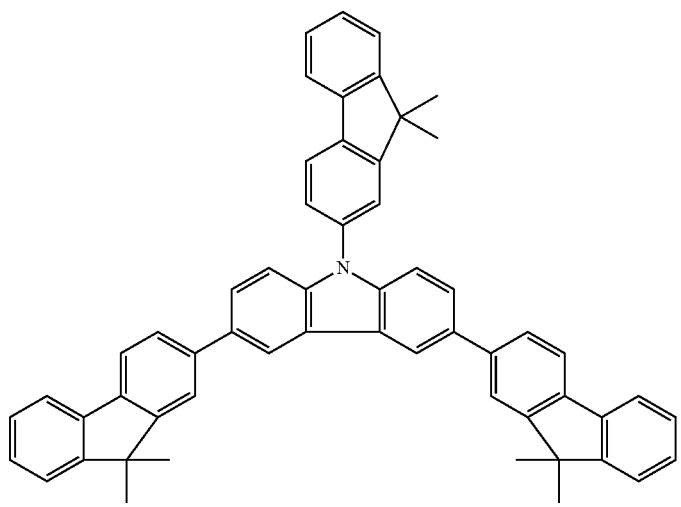 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18
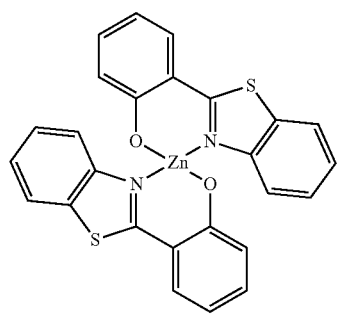
H19
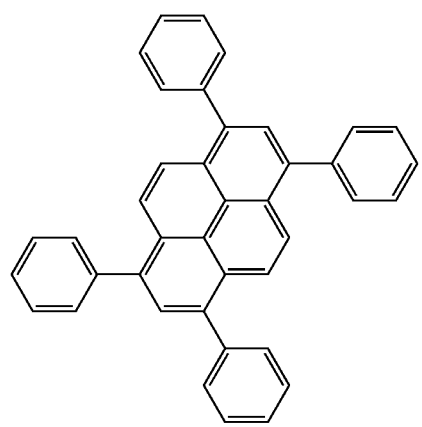 [SMILES: c1ccc(-c2cc(-c3ccccc3)c3ccc4c(-c5ccccc5)cc(-c5ccccc5)c5ccc2c3c54)cc1]
H20
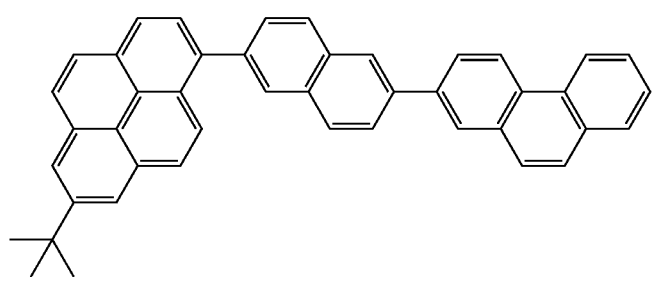 [SMILES: CC(C)(C)c1cc2ccc3ccc(-c4ccc5cc(-c6ccc7c(ccc8ccccc87)c6)ccc5c4)c4ccc(c1)c2c34]
H21

TABLE 2-continued
| | |
|---|---|
| 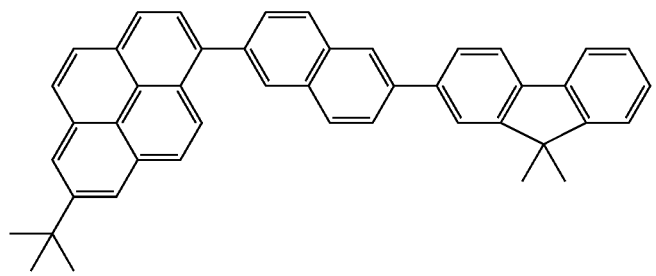 [SMILES: CC(C)(C)c1cc2ccc3ccc(-c4ccc5cc(-c6ccc7c(c6)C(C)(C)c6ccccc6-7)ccc5c4)c4ccc(c1)c2c34] | H22 |
| 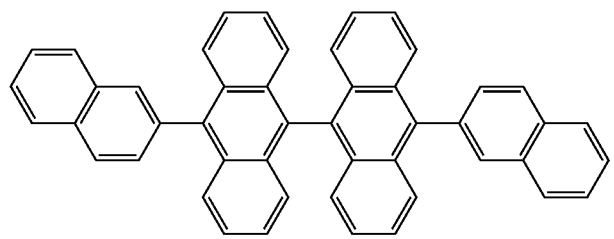 [SMILES: c1ccc2cc(-c3c4ccccc4c(-c4c5ccccc5c(-c5ccc6ccccc6c5)c5ccccc45)c4ccccc34)ccc2c1] | H23 |
| 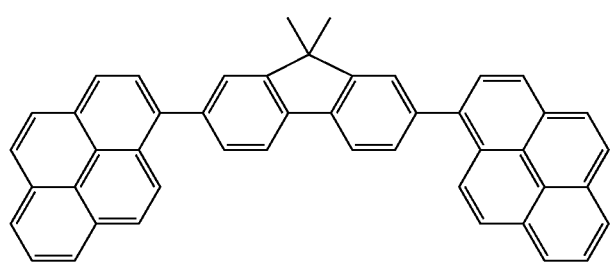 [SMILES: CC1(C)c2cc(-c3ccc4ccc5cccc6ccc3c4c56)ccc2-c2ccc(-c3ccc4ccc5cccc6ccc3c4c56)cc21] | H24 |
| 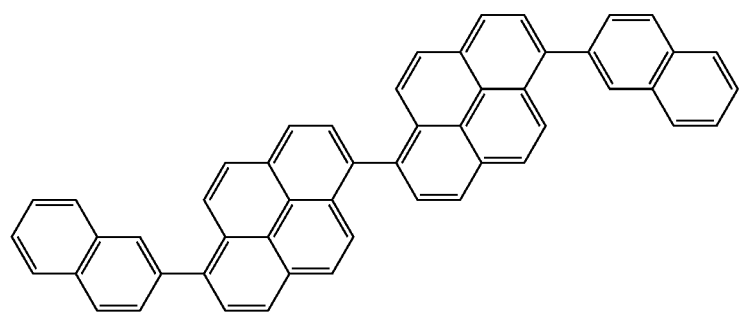 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1] | H25 |
| 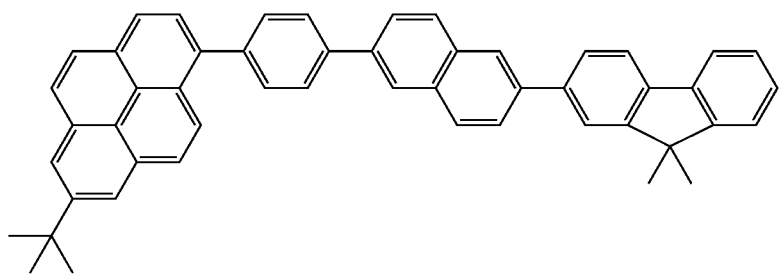 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34] | H26 |
| 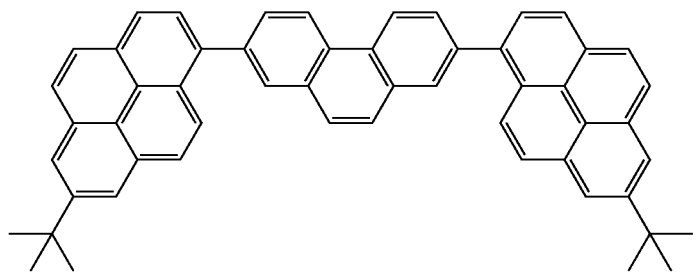 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34] | H27 |

TABLE 2-continued

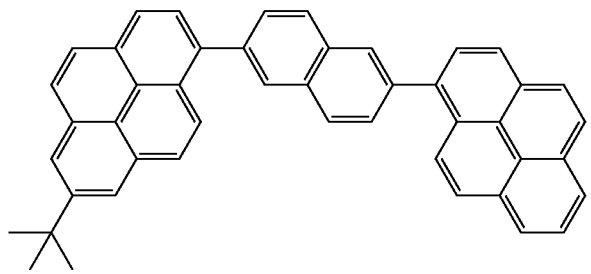 [SMILES: CC(C)(C)c1cc2ccc3ccc(-c4ccc5cc(-c6ccc7ccc8cccc9ccc6c7c89)ccc5c4)c4ccc(c1)c2c34]

H28

The electron injection materials or the electron-transporting materials are selected in consideration of, for example, the balance with the hole mobility of the hole injection materials or the hole-transporting materials. Examples of the materials having an electron injection performance or an electron transport performance include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

As anode materials, those having a work function as high as possible are preferable. Examples of the anode materials include metal elements such as gold, platinum, silver, copper, nickel, palladium, cobalt, selenium, vanadium, and tungsten; alloys thereof; and metal oxides such as tin oxide, zinc oxide, indium oxide, indium tin oxide (ITO), and indium zinc oxide. In addition, electrically conductive polymers such as polyaniline, polypyrrole, and polythiophene may also be used. These electrode materials may be used alone or in combinations of two or more materials. The anode may have a single-layer structure or a multi-layer structure.

On the other hand, as cathode materials, those having a low work function are preferable. Examples of the cathode materials include metal elements such as alkali metals, e.g., lithium; alkaline earth metals, e.g., calcium; aluminum; titanium; manganese; silver; lead; and chromium. Alloys combining these metal elements may also be used. For example, magnesium-lithium, aluminum-lithium, or aluminum-magnesium can be used. Metal oxides such as indium tin oxide (ITO) may also be used. These electrode materials may be used as alone or in combinations of two or more materials. The cathode may have a single-layer structure or a multi-layer structure.

In the organic light-emitting device of this embodiment, a layer containing the organic compound according to the present invention and layers composed of the other organic compounds are formed by the methods described below. In general, each of the layers is formed by a vacuum evaporation method, an ionized evaporation method, a sputtering method, a method using plasma, or a known coating method (for example, spin coating, dipping, a cast method, a Langmuir Blodgett (LB) method, or an ink jet method) after a material is dissolved in a suitable solvent. Among these, when a layer is formed by, for example, the vacuum evaporation method or the solution coating method, crystallization does not tend to occur, and thus the resulting layer has good stability with time. When a layer is formed by the coating method, the material may be used in combination with a suitable binder resin.

Examples of the binder resin include, but are not limited to, polyvinylcarbazole resins, polycarbonate resins, polyester resins, acrylonitrile butadiene styrene (ABS) resins, acrylic resins, polyimide resins, phenolic resins, epoxy resins, silicone resins, and urea resins. These binder resins may be used alone as a homopolymer or a copolymer or used as a mixture of two or more types of resins. Furthermore, additives such as a known plasticizer, antioxidant, or ultraviolet absorber may be optionally used in combination.

Apparatus Including Organic Light-Emitting Device

An apparatus including an organic light-emitting device according to this embodiment will now be described.

The organic light-emitting device according to this embodiment can be used in a display apparatus or an illuminating device. In addition, the organic light-emitting device according to this embodiment can be used in an exposure light source of an electrophotographic image-forming apparatus or a backlight of a liquid crystal display apparatus.

The display apparatus includes a display unit including the organic light-emitting device according to this embodiment. This display unit includes a plurality of pixels. Each of the pixels includes the organic light-emitting device according to this embodiment and a thin-film transistor (TFT) device which is an example of a switching device. An anode or a cathode of this organic light-emitting device is connected to a drain electrode or a source electrode of the TFT device. The display apparatus can be used as an image display apparatus such as a personal computer (PC). The display apparatus may be an image input apparatus that further includes an image input unit.

The image input apparatus includes an image input unit to which information from an area CCD sensor, a linear CCD sensor, a memory card, or the like is input and a display unit configured to display the input information. Such an image input apparatus that further includes an imaging optical system constitutes an image pickup apparatus such as a digital camera. The display unit of such an image pickup apparatus or an ink jet printer may have both an image output function of displaying an image on the basis of image information input from the outside and an input function, as an operation panel, of inputting process information to the image. The display apparatus may be used as a display unit of a multi-function printer.

Next, a display apparatus including the organic light-emitting device according to this embodiment will be described. FIG. 1 is a schematic cross-sectional view of a display apparatus including organic light-emitting devices according to this embodiment and TFT devices which are an example of switching devices configured to switch emission/non-emission of the organic light-emitting devices. FIG. 1 shows two pairs of an organic light-emitting device and a TFT device. Although not shown in the figure, the display device may further include a transistor configured to control the light-emission luminance. The display apparatus performs a display by turning on or turning off the organic light-emitting devices by driving the switching devices in accordance with information, and transmit the information. The detailed structure of the display apparatus will be described below.

The display apparatus shown in FIG. 1 includes a substrate 1 composed of, for example, glass and a moisture-proof film 2 for protecting TFT devices or organic compound layers, the moisture-proof film 2 being disposed on the substrate 1. Reference numeral 3 indicates a metal gate electrode, reference numeral 4 indicates a gate insulating film, and reference numeral 5 indicates a semiconductor layer.

TFT devices 8 each include the semiconductor layer 5, a drain electrode 6, and a source electrode 7. An insulating film 9 is provided on the upper portion of the TFT devices 8. An anode 11 of an organic light-emitting device is connected to the source electrode 7 through a contact hole 10. However, the structure of the display apparatus is not limited to this. It is sufficient that either the anode or the cathode of the organic light-emitting device is connected to either the source electrode or the drain electrode of a TFT device.

In FIG. 1, a plurality of organic compound layers are shown as a single organic compound layer 12. A first protective layer 14 and a second protective layer 15 for suppressing degradation of the organic light-emitting devices are provided on a cathode 13.

EXAMPLES

Example 1

Synthesis of Exemplary Compound A2

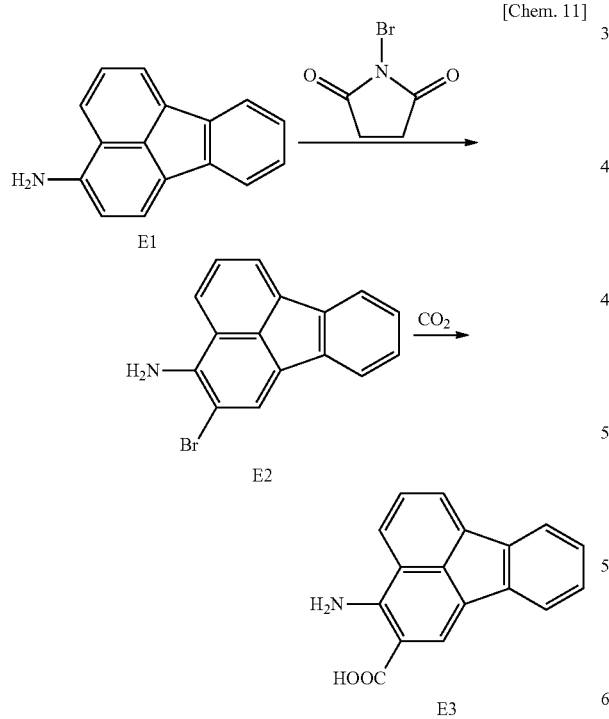

First, 10.5 g (48 mmol) of fluoranthene-3-amine (E1) was mixed with 300 mL of dimethylformamide at 0 degrees (Celsius). Next, 8.2 g (48 mmol) of N-bromosuccinimide was added to the mixture. The temperature was returned to room temperature, and the reaction mixture was stirred for eight hours. The reaction mixture was poured into water, and a precipitate was filtered. The precipitate was then recrystallized with ethanol. The resulting crystals were filtered, washed with heptane, and then dried. Thus, 29 g of a brown solid E2 was obtained (yield: 60%). Subsequently, 10 g (34 mmol) of E2 was put in a 500-mL round-bottom flask, and the inside of the reaction system was replaced with argon. Next, 150 mL of methoxycyclopentane was put in the flask in an argon atmosphere, and the solution was cooled to −75 degrees (Celsius). Next, 64 mL of a 1.6 M solution of n-butyllithium was added dropwise thereto. After the dropwise addition, the temperature of the reaction mixture was returned to room temperature, and stirring was conducted for one hour. Subsequently, the reaction mixture was again cooled to −75 degrees (Celsius), and 15 g of finely crushed dry ice was added to the mixture. The temperature of the reaction mixture was gradually returned to room temperature. After the temperature was returned to room temperature, stirring was conducted for eight hours, and 1 M hydrochloric acid was then added to the reaction mixture to terminate the reaction. Subsequently, extraction was conducted with ethyl acetate. The organic layer was concentrated to obtain a brown liquid. The liquid was purified by column chromatography (ethyl acetate/heptane=1:3), and recrystallized with chloroform/methanol. Thus, 2.5 g of E3 was obtained in the form of a brown powder (yield: 28%).

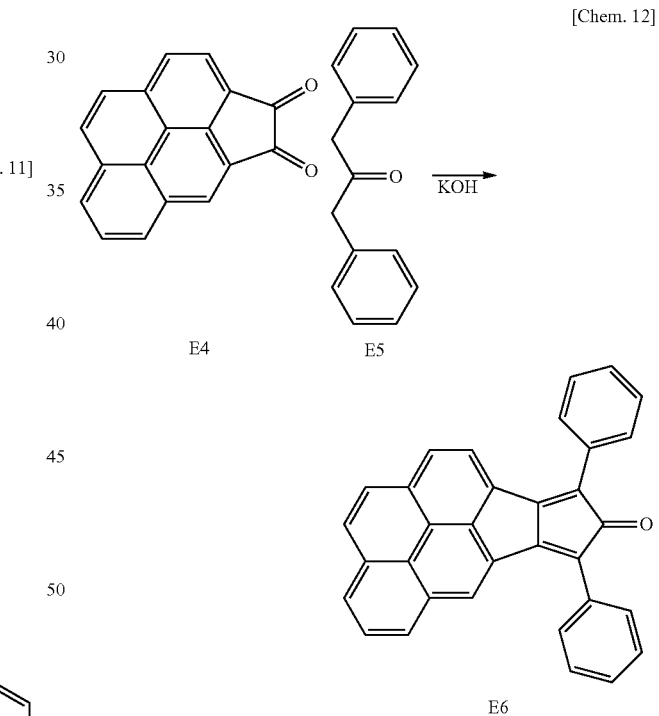

Next, 12.8 g (50 mmol) of E4 and 10.5 g (50 mmol) of E5 were put in 200 mL of ethanol, and the resulting mixture was heated to 60 degrees (Celsius). Subsequently, 20 mL of a 5 M aqueous potassium hydroxide solution was added dropwise thereto. After the dropwise addition, the reaction mixture was heated to 80 degrees (Celsius), stirring was conducted for two hours, and the reaction mixture was cooled. A precipitate was then filtered, and washed with water and ethanol. The precipitate was then dried by heating under reduced pressure at 80 degrees (Celsius). Thus, 18 g of a dark green solid E6 was obtained (yield: 85%).

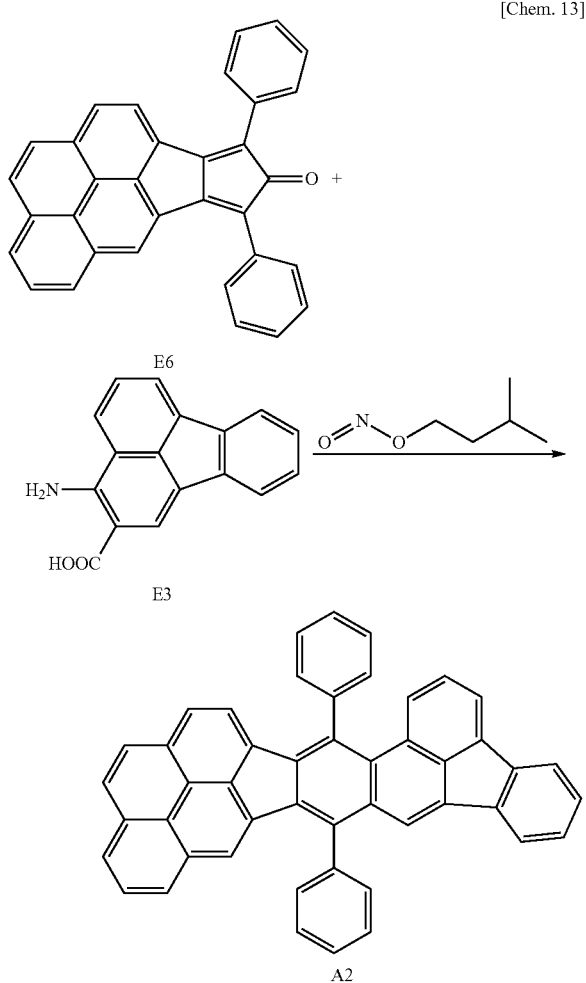

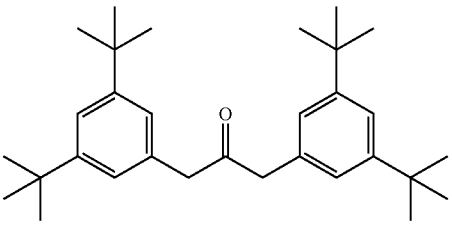

Example 1 except that the organic compound E5 used in Example 1 was changed to an organic compound E7.

[Chem. 14]

An emission spectrum of a toluene solution of Exemplary compound A3 with a concentration of $1\times10^{-5}$ mol/L was obtained by measuring photoluminescence at an excitation wavelength of 350 nm using a fluorescence spectrophotometer F-4500 produced by Hitachi, Ltd. According to the measurement result, the spectrum had a maximum intensity at 488 nm.

Example 3

Synthesis of Exemplary Compound A4

Exemplary compound A4 was obtained by the same reactions and purification procedures as those performed in Example 1 except that the organic compound E5 used in Example 1 was changed to an organic compound E8.

[Chem. 15]

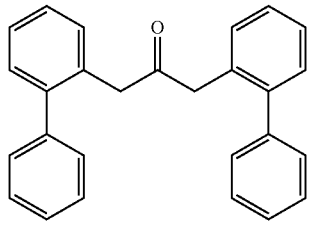

Next, 2.1 g (5 mmol) of E6 and 1.57 g (6 mmol) of E3 were put in 50 mL of toluene, and the mixture was heated to 80 degrees (Celsius). Subsequently, 0.82 g (7 mmol) of isoamyl nitrite was then slowly added dropwise to the mixture. The reaction mixture was then stirred at 110 degrees (Celsius) for three hours. The reaction mixture was cooled, and washed with 100 mL of water twice. The resulting organic layer was washed with a saturated saline solution, and dried with magnesium sulfate. Subsequently, the resulting solution was filtered, and the filtrate was then concentrated to obtain a brown liquid. This liquid was purified by column chromatography (chloroform/heptane=1:3), and recrystallized with chloroform/methanol. Thus, 2.3 g of A2 was obtained in the form of yellow crystals (yield: 76%).

An emission spectrum of a toluene solution of Exemplary compound A2 with a concentration of $1\times10^5$ mol/L was obtained by measuring photoluminescence at an excitation wavelength of 350 nm using a fluorescence spectrophotometer F-4500 produced by Hitachi, Ltd. According to the measurement result, the spectrum had a maximum intensity at 487 nm.

Example 2

Synthesis of Exemplary Compound A3

Exemplary compound A3 was obtained by the same reactions and purification procedures as those performed in An emission spectrum of a toluene solution of Exemplary compound A4 with a concentration of $1\times10^{-5}$ mol/L was obtained by measuring photoluminescence at an excitation wavelength of 350 nm using a fluorescence spectrophotometer F-4500 produced by Hitachi, Ltd. According to the measurement result, the spectrum had a maximum intensity at 488 nm.

Example 4

Synthesis of Exemplary Compound A14

Exemplary compound A14 was obtained by the same reactions and purification procedures as those performed in Example 1 except that the organic compound E4 used in Example 1 was changed to an organic compound E9, and that the organic compound E5 used in Example 1 was changed to the organic compound E7.

[Chem. 16]

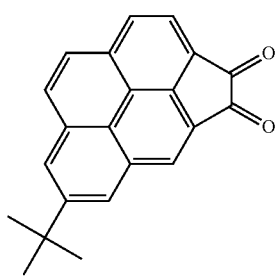

E9

An emission spectrum of a toluene solution of Exemplary compound A14 with a concentration of $1\times10^{-5}$ mol/L was obtained by measuring photoluminescence at an excitation wavelength of 350 nm using a fluorescence spectrophotometer F-4500 produced by Hitachi, Ltd. According to the measurement result, the spectrum had a maximum intensity at 490 nm.

Examples 5 to 12

Fabrication of Organic Light-Emitting Devices

In each of Examples 5 to 12, an organic light-emitting device having a structure in which an anode, a hole-transporting layer, a light-emitting layer, a hole/exciton-blocking layer, an electron-transporting layer, and a cathode were sequentially stacked was fabricated. First, an ITO film having a thickness of 100 nm was patterned on a glass substrate. On the substrate having the ITO film thereon, the following organic layers and electrode layers were successively deposited by a resistance-heating vacuum evaporation method in a vacuum chamber at a pressure of $10^{-5}$ Pa so that the area of the facing electrodes was 3 mm².

Hole-transporting layer (40 nm): G-1

Light-emitting layer (30 nm); Host: G-2, Guest: Exemplary compound (weight ratio 5%)

Hole/exciton-blocking layer (10 nm): G-3

Electron-transporting layer (30 nm): G-4

Metal electrode layer 1 (1 nm): LiF

Metal electrode layer 2 (100 nm): Al

[Chem. 17]

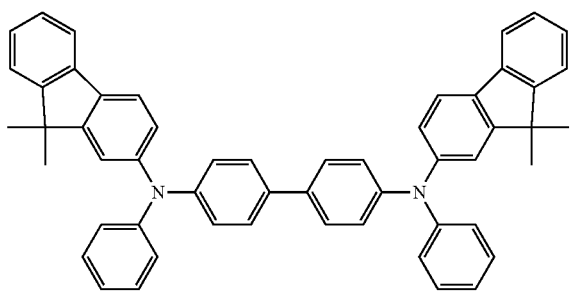

G-1

-continued

G-3

G-4

As for characteristics of the organic light-emitting devices, current-voltage characteristics were measured with a micrometer 4140B manufactured by Hewlett-Packard Development Company, and the light-emission luminance was measured with a luminance meter BM7 manufactured by Topcon Corporation. The quantum yields and the voltages of Examples 5 to 12 are shown in Table 3.

TABLE 3

| | Guest | G-2 | Quantum yield (cd/A) | Voltage (V) |
|---|---|---|---|---|
| Example 5 | A2 | H7 | 12 | 4.7 |
| Example 6 | A2 | H10 | 14 | 4.7 |
| Example 7 | A3 | H10 | 14 | 4.6 |
| Example 8 | A3 | H28 | 15 | 4.8 |
| Example 9 | A13 | H17 | 12 | 4.6 |
| Example 10 | A14 | H4 | 16 | 4.8 |
| Example 11 | A22 | H26 | 14 | 4.6 |
| Example 12 | A31 | H13 | 12 | 4.7 |

Examples 13 to 16

In each of Examples 13 to 16, an organic light-emitting device having a structure in which an anode, a hole injection layer, a hole-transporting layer, a light-emitting layer, an electron-transporting layer, and an electron injection layer, and a cathode were sequentially stacked was fabricated.

The organic light-emitting device having a resonance structure was fabricated by the method described below. An aluminum alloy (AlNd) film having a thickness of 100 nm and functioning as a reflective anode was deposited on a glass substrate functioning as a support by a sputtering method. Furthermore, an ITO film having a thickness of 80 nm and functioning as a transparent anode was formed by a sputtering method. Next, an element isolation film composed of a polyimide resin and having a thickness of 1.5 micrometers was formed on the periphery of the anode, and an opening having a radius of 3 mm was formed. The substrate was sequentially subjected to ultrasonic washing with acetone and isopropyl alcohol (IPA). The substrate was then washed in boiling IPA, and dried. The surface of this substrate was further subjected to UV cleaning.

Furthermore, the following organic compounds were successively deposited by a resistance-heating vacuum evaporation method in a vacuum chamber at a pressure of $10^{-5}$ Pa. Subsequently, indium zinc oxide (IZO) was deposited as a cathode by a sputtering method, thus forming a transparent electrode having a thickness of 30 nm. After the formation of this electrode, sealing was performed in a nitrogen atmosphere. Thus, the organic light-emitting devices were fabricated.

Hole injection layer (135 nm): G-11
Hole-transporting layer (10 nm): G-12
Light-emitting layer (35 nm); Host: G-13, Guest: Exemplary compound (weight ratio 2%)
Electron-transporting layer (10 nm): G-14
Electron injection layer (70 nm): G-15 (weight ratio 80%), Li (weight ratio 20%)

[Chem. 18]

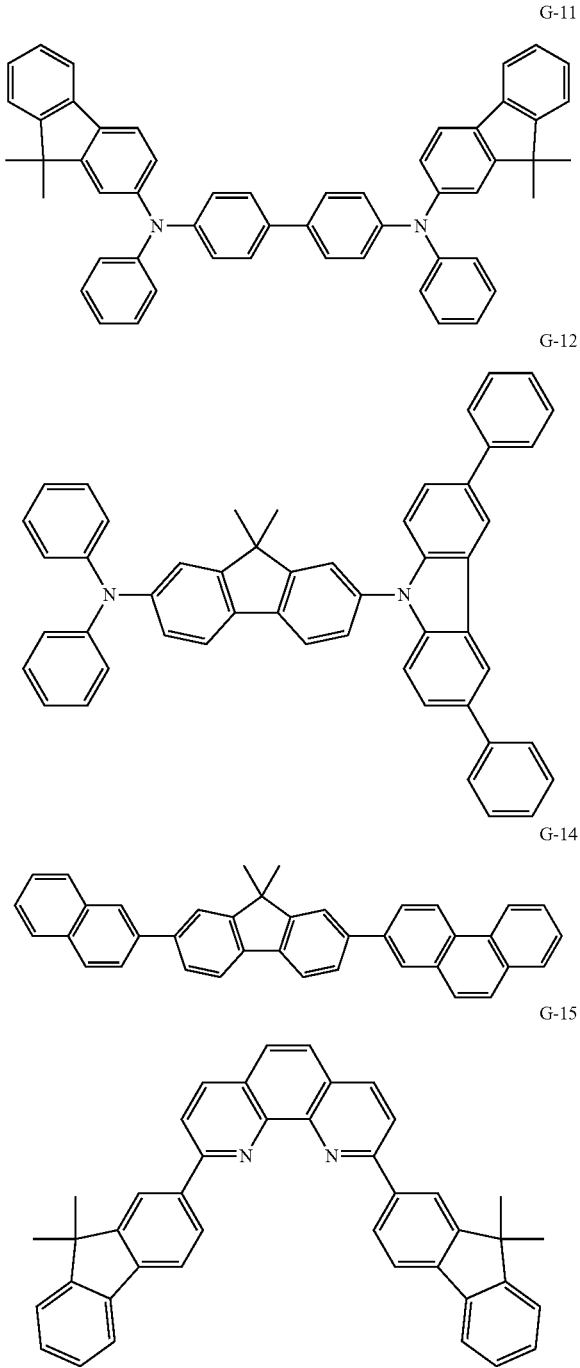

As for characteristics of the organic light-emitting devices, current-voltage characteristics were measured with a microammeter 4140B manufactured by Hewlett-Packard Development Company, and the light-emission luminance was measured with a luminance meter BM7 manufactured by Topcon Corporation. The quantum yields and the voltages of Examples 13 to 16 are shown in Table 4.

TABLE 4

| | Guest | G-13 | Quantum yield (cd/A) | Voltage (V) |
|---|---|---|---|---|
| Example 13 | A3 | H7 | 19 | 4.5 |
| Example 14 | A4 | H28 | 18 | 4.5 |
| Example 15 | A14 | H27 | 15 | 4.7 |
| Example 16 | A22 | H24 | 17 | 4.7 |

Results and Discussion

The organic compound according to the present invention is a novel compound that has a high quantum yield and that realizes light emission suitable for green light. When the organic compound according to the present invention is used in an organic light-emitting device, a light-emitting device having good light-emission characteristics can be fabricated.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-078291, filed Mar. 30, 2010, which is hereby incorporated by reference herein in its entirety.

REFERENCE SIGNS LIST

8 TFT device
11 Anode
12 Organic compound layer
13 Cathode

The invention claimed is:
1. An organic compound represented by general formula (1):

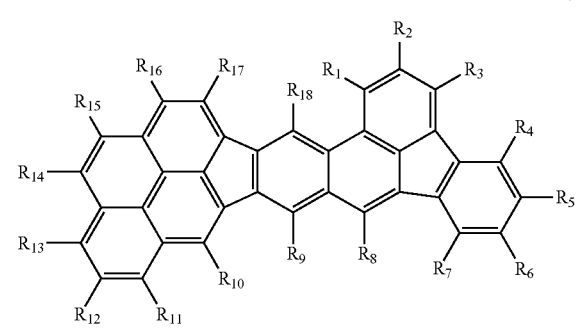

wherein $R_1$ to $R_{18}$ are each independently selected from a hydrogen atom, a halogen atom, a substituted or unsubstituted alkyl group, a substituted or unsubstituted alkoxy group, a substituted amino group, a substituted or unsubstituted aryl group, and a substituted or unsubstituted heterocyclic group.

2. The organic compound according to claim 1, wherein $R_1$ to $R_{18}$ are each independently selected from a hydrogen atom, a substituted or unsubstituted alkyl group having 1 to 4 carbon atoms, and a substituted or unsubstituted aryl group.

3. The organic compound according to claim 2, wherein the organic compound is represented by general formula (2):

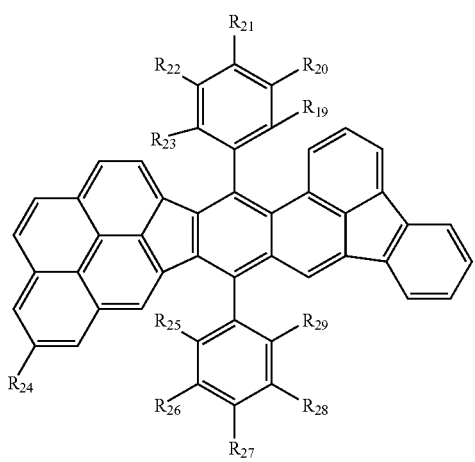

(2)

wherein $R_{19}$ to $R_{29}$ are each independently selected from a hydrogen atom, a substituted or unsubstituted alkyl group having 1 to 4 carbon atoms, and a substituted or unsubstituted phenyl group.

4. An organic light-emitting device comprising:
a pair of electrodes; and
an organic compound layer disposed between the pair of electrodes,
wherein the organic compound layer contains the organic compound according to claim 1.

5. The organic light-emitting device according to claim 4, wherein the organic compound layer is a light-emitting layer.

6. The organic light-emitting device according to claim 5, wherein the organic light-emitting device emits green light.

7. A display device comprising:
a plurality of pixels,
wherein the plurality of pixels each include the organic light-emitting device according to claim 4 and a switching device connected to the organic light-emitting device.

8. An image input apparatus comprising:
a display unit configured to display an image; and
an image input unit configured to input the image,
wherein the display unit includes a plurality of pixels, and the plurality of pixels each include the organic light-emitting device according to claim 4 and a switching device connected to the organic light-emitting device.

9. An illuminating apparatus comprising the organic light-emitting device according to claim 4.

10. An electrophotographic image-forming apparatus comprising an exposure light source;
wherein the exposure light source comprises the organic light-emitting device according to claim 4.

11. An exposure light source of an electrophotographic image-forming apparatus comprising the organic light-emitting device according to claim 4.

* * * * *